United States Patent
Schroeter et al.

(10) Patent No.: US 11,173,479 B2
(45) Date of Patent: Nov. 16, 2021

(54) METHOD FOR PRODUCING A SHAPED CATALYST BODY

(71) Applicant: BASF SE, Ludwigshafen am Rhein (DE)

(72) Inventors: Marie Katrin Schroeter, Ludwigshafen (DE); Irene de Wispelaere, Antwerp (BE); Michael Schwarz, Ludwigshafen (DE); Rolf Pinkos, Ludwigshafen (DE); Inna Schwabauer, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/648,502

(22) PCT Filed: Sep. 10, 2018

(86) PCT No.: PCT/EP2018/074298
§ 371 (c)(1),
(2) Date: May 4, 2020

(87) PCT Pub. No.: WO2019/057533
PCT Pub. Date: Mar. 28, 2019

(65) Prior Publication Data
US 2020/0269227 A1    Aug. 27, 2020

(30) Foreign Application Priority Data

Sep. 20, 2017   (EP) .................................... 17192179

(51) Int. Cl.
| C07C 29/141 | (2006.01) |
| B01J 37/00 | (2006.01) |
| B01J 21/04 | (2006.01) |
| B01J 23/755 | (2006.01) |
| B01J 35/04 | (2006.01) |
| B01J 37/02 | (2006.01) |
| B01J 37/08 | (2006.01) |
| B01J 37/18 | (2006.01) |
| C07C 29/17 | (2006.01) |

(52) U.S. Cl.
CPC ........... *B01J 37/0018* (2013.01); *B01J 21/04* (2013.01); *B01J 23/755* (2013.01); *B01J 35/04* (2013.01); *B01J 37/0225* (2013.01); *B01J 37/08* (2013.01); *B01J 37/18* (2013.01); *C07C 29/141* (2013.01); *C07C 29/172* (2013.01)

(58) Field of Classification Search
CPC .. C07C 29/141; C07C 29/172; B01J 37/0018; B01J 37/08
See application file for complete search history.

(56) References Cited

U.S. PATENT DOCUMENTS

| 1,563,587 | A | 12/1925 | Raney |
| 1,628,190 | A | 5/1927 | Raney |
| 1,915,473 | A | 6/1933 | Raney |
| 2,895,819 | A | 7/1959 | Fiedler |
| 3,448,060 | A | 6/1969 | Mason |
| 6,121,188 | A | 9/2000 | Breitscheidel et al. |
| 6,747,180 | B2 | 6/2004 | Ostgard et al. |
| 2009/0018366 | A1 | 1/2009 | Berweiler et al. |
| 2014/0221700 | A1* | 8/2014 | Radivojevic ......... B01J 37/0018 568/885 |
| 2019/0210010 | A1 | 7/2019 | Pinkos et al. |
| 2019/0344248 | A1 | 11/2019 | Pinkos et al. |
| 2020/0016579 | A1 | 1/2020 | Schreiber et al. |
| 2020/0016583 | A1 | 1/2020 | Merkel et al. |

FOREIGN PATENT DOCUMENTS

| CN | 101254466 A | 9/2008 |
| EP | 0842699 A2 | 5/1998 |
| EP | 1068900 A1 | 1/2001 |
| EP | 1125634 A1 | 8/2001 |
| EP | 2764916 A1 | 8/2014 |
| EP | 3515593 A1 | 7/2019 |
| EP | 3515594 A1 | 7/2019 |
| EP | 3515597 A1 | 7/2019 |
| WO | 2019048279 A1 | 3/2019 |

OTHER PUBLICATIONS

European Search Report for EP Patent Application No. 17192179.4, dated Mar. 6, 2018, 3 pages.
International Search Report for Application No. PCT/EP2018/074298, dated Nov. 19, 2018, 2 pages.

\* cited by examiner

*Primary Examiner* — Sikarl A Witherspoon
(74) *Attorney, Agent, or Firm* — Armstrong Teasdale LLP

(57) ABSTRACT

Provided herein is a novel process for producing shaped catalyst bodies in which a mixture having aluminum contents of $Al^0$ in the range from 80 to 99.8% by weight, based on the mixture used, is used to form a specific intermetallic phase, shaped catalyst bodies obtainable by the process of the invention, a process for producing an active catalyst fixed bed including the shaped catalyst bodies provided herein, the active catalyst fixed beds and also the use of these active catalyst fixed beds for the hydrogenation of organic hydrogenatable compounds or for formate degradation.

16 Claims, 3 Drawing Sheets

FIG. 1: Shaped Ni-Al bodies after step b), produced using a mixture comprising 86% by weight of Al (70% of $Al^{\pm 0}$, 16% of $Al^{3+}$)
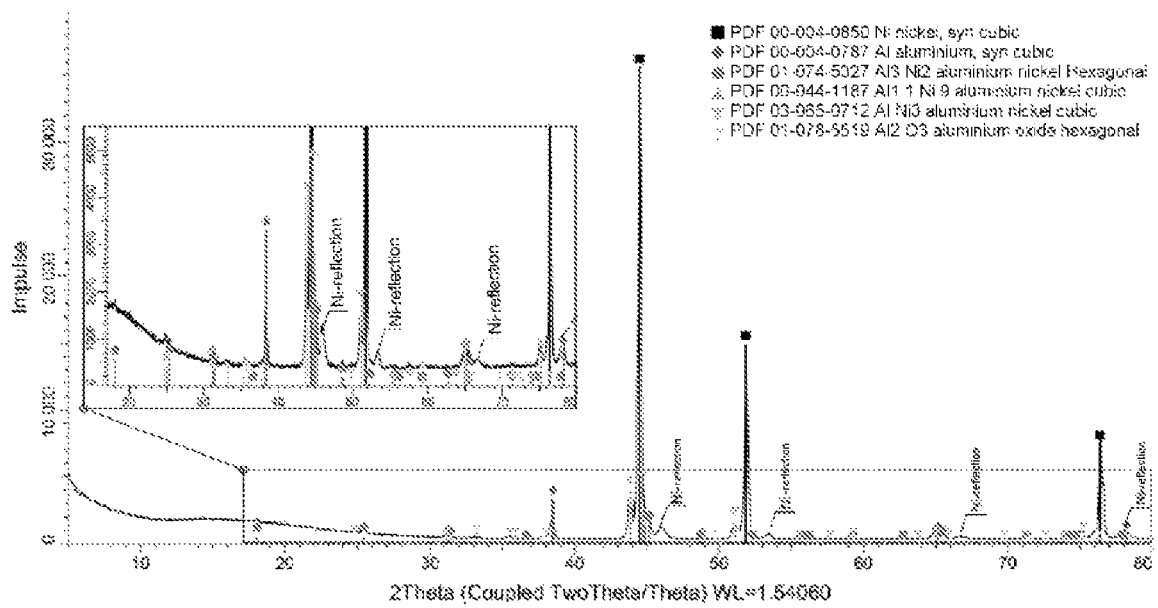

Fig 2: Shaped Ni-Al body after step b), produced using a mixture comprising 88% by weight of Al (74.6% of $Al^{\pm 0}$, 13.4% of $Al^{3+}$)
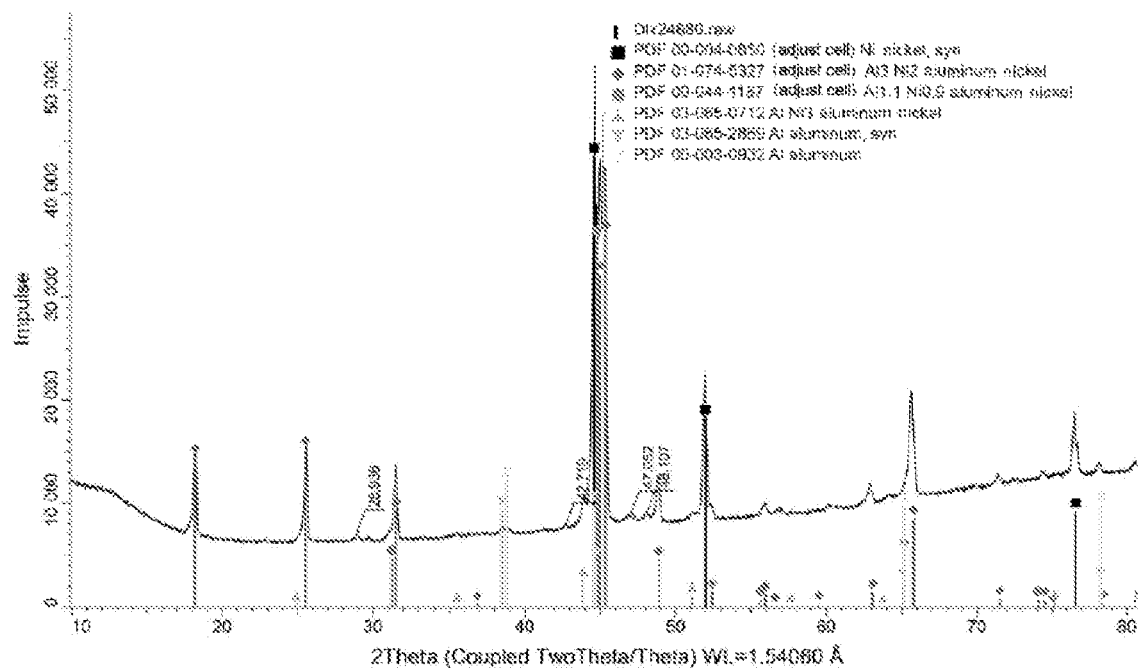

Fig 3: Shaped Ni-Al bodies after step b), produced using a mixture comprising 99% by weight of Al (97.9% of $Al^{\pm 0}$, 1.1% of $Al^{3+}$)
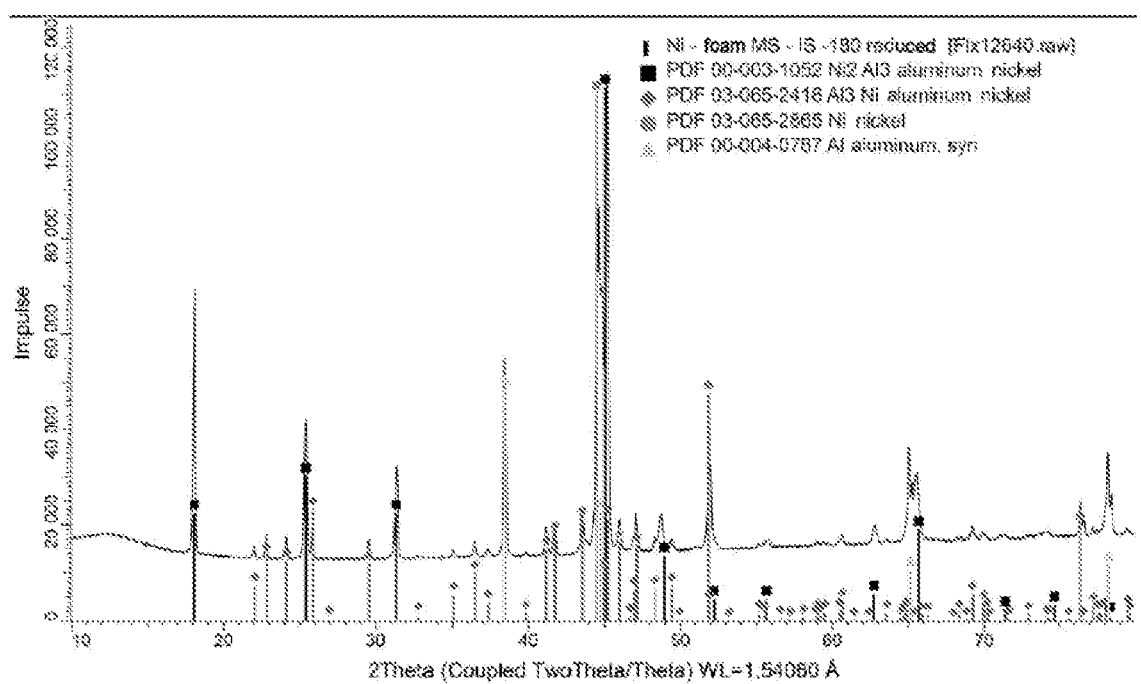
[Ni – foam MS – IS – 180 reduced [Flx12640.raw]
lower case   aluminum nickel
WL = 1.54060 Å

METHOD FOR PRODUCING A SHAPED CATALYST BODY

BACKGROUND OF THE INVENTION

The present invention relates to a novel process for producing shaped catalyst bodies in which a mixture having aluminum contents of $Al^{\pm 0}$ in the range from 80 to 99.8% by weight, based on the mixture used, is used to form a specific intermetallic phase, shaped catalyst bodies obtainable by the process of the invention, a process for producing an active catalyst fixed bed comprising the shaped catalyst bodies of the invention, the active catalyst fixed beds and also the use of these active catalyst fixed beds for the hydrogenation of organic hydrogenatable compounds or for formate degradation.

PRIOR ART

Raney metal catalysts or activated porous metal catalysts are highly active catalysts which have found wide commercial use. The precursor for Raney catalysts is usually an alloy/intermetallic phase comprising at least one catalytically active metal and at least one alkali-soluble (leachable) alloying component. Typical catalytically active metals are, for example, Ni, Co, Cu, with additions of Fe, Cr, Pt, Ag, Au, Mo and Pd and typical leachable alloying components are, for example, Al, Zn and Si. Such Raney metal catalysts and processes for the production thereof are described, for example, in U.S. Pat. Nos. 1,628,190, 1,915,473 and 1,563,587.

The production of the Raney metal from the alloys is generally carried out by an activating process in which the leachable component is removed by use of concentrated sodium hydroxide solution. The removal is not complete. Remaining species of, for example, Al can contribute to stabilization of the structure of the highly porous Raney metal powders. However, depending on the use in catalysis, the remaining Al species can come away from the catalyst further, change in the reaction medium (for example formation of boehmite) and thus adversely affect the mechanical stability and the performance of the catalyst.

A critical disadvantage of pulverulent Raney metal catalysts is the necessity of separating them off from the reaction medium of the catalyzed reaction by costly sedimentation and/or filtration processes. A further disadvantage is the mechanical stressing of the catalyst by use of a stirrer, a pump or the like.

Raney metal catalysts are also used in the form of larger particles. Thus, U.S. Pat. No. 3,448,060 describes the production of structured Raney metal catalysts, in which, in a first embodiment, an inert support material is coated with an aqueous suspension of a pulverulent nickel-aluminum alloy and freshly precipitated aluminum hydroxide. The structure obtained in this way is dried, heated and brought into contact with water, resulting in hydrogen being liberated. The structure is subsequently hardened. Leaching with an alkali metal hydroxide solution is optionally provided. In a second embodiment, an aqueous suspension of a pulverulent nickel-aluminum alloy and freshly precipitated aluminum hydroxide is subjected to shaping without use of a support material. The resulting structure is activated in a manner analogous to the first embodiment.

Further Raney metal catalysts suitable for use in fixed-bed catalysts can comprise hollow bodies or spheres or be supported in another way. Such catalysts are, for example, described in EP 0 842 699, EP 1 068 900, U.S. Pat. Nos. 6,747,180, 2,895,819 and US 2009/0018366.

EP 1 125 634 describes a process for dehydrogenating alcohols using shaped bodies composed of Raney copper. The catalysts are produced here from an alloy powder comprising 50% of Al and 50% of Cu. Auxiliaries are added and the powder is pressed to give, for example, 3×3 mm pellets or a hollow body is produced.

EP 2 764 916 describes a process for producing foam-like shaped catalyst bodies which are suitable for hydrogenations, in which:
a) a shaped metal foam body comprising at least one first metal selected, for example, from among Ni, Fe, Co, Cu, Cr, Pt, Ag, Au and Pd is provided,
b) at least one second leachable component or a component which can be converted by alloying into a leachable component, for example selected from among Al, Zn and Si, is applied to the surface of the shaped metal foam body and
c) an alloy is formed at least on part of the surface by alloying of the shaped metal foam body obtained in step b) and
d) the foam-like alloy obtained in step c) is subjected to treatment with an agent which is capable of leaching out the leachable components of the alloy.

The second leachable component is in this case a metal or an intermetallic compound. No aluminum contents of the intermetallic compound used are disclosed in the description. To activate the alloy obtained in step c), the shaped metal foam bodies are treated with at least 1 to 10 M NaOH, corresponding to an aqueous NaOH solution having a concentration of at least 3.9% by weight.

In the abovementioned examples of EP 2 764 916, metallic Al powder is used. The handling of 100% $Al^{\pm 0}$ as powder incurs a high risk. It is highly combustible in air and reacts vigorously with acids, alkalis and water to liberate highly flammable hydrogen. Vigorous reactions also occur with oxidants and contact with halogens or monohalogenated hydrocarbons can lead to vigorous reaction with formation of, for example, hydrochloric acid vapors. The use of 100% $Al^{\pm 0}$ as powder is therefore unsuitable for the industrial production of such foam bodies. EP 16190425.5, EP16190427.1 and EP161.90428.9 likewise describe processes for providing catalyst fixed beds which likewise comprise foam-like shaped catalyst bodies comprising at least one metal selected from the group consisting of Ni, Fe, Co, Cu, Cr, Pt, Ag, Au and Pd which are then impregnated further with a second component, where the second component is selected from the group consisting Al, Zn and Si, and the catalyst bodies are subsequently activated by means of an aqueous base and used for hydrogenations of organic hydrogenatable compounds. However, no aluminum contents of the second component are disclosed here and the hydrogenations disclosed in the examples can also only be operated at low space velocities over the catalyst. No indication that a specific content of $Al^{\pm 0}$ has to be comprised in the second component in order to achieve higher space velocities over the catalyst while maintaining the same conversion, yield and selectivity is described.

SUMMARY OF THE INVENTION

It has now surprisingly been found that the production of shaped catalyst bodies using a mixture comprising from 80 to 99.8% by weight of $Al^{\pm 0}$, based on the mixture, as second component and subsequent thermal treatment and activation of the resulting shaped catalyst bodies in the catalyst fixed bed enables equally good conversions, yields and selectivities for hydrogenations as described in the prior art to be achieved. However, several times higher space velocities over the catalyst can at the same time be achieved using such catalyst fixed beds than would have been possible in the case of shaped catalyst bodies and suspended catalysts according to the prior art.

It is therefore an object of the present invention to provide a process which makes it possible to provide shaped catalyst bodies which achieve, after activation in a catalyst fixed bed, similarly good conversions, yields and selectivities in hydrogenations of organic hydrogenatable compounds as is known in the prior art and at the same time realize several times higher space velocities over the catalyst.

This object is achieved by a process for producing a shaped catalyst body, comprising the following steps:

a) provision of a shaped metal foam body comprising at least one first metal selected from the group consisting of Ni, Fe, Co, Cu, Cr, Pt, Ag, Au and Pd, and b) impregnation of the surface of the shaped metal foam body with
   b1) a binder and
   subsequently or simultaneously with a mixture as second component, where the mixture comprises from 80 to 99.8% by weight of $Al^{\pm 0}$, based on the mixture, and c) thermal treatment under reducing conditions of the impregnated shaped metal foam body obtained in step b) so that intermetallic phases in the form of alloys of the metal of the monolithic shaped metal foam body from step a) and the aluminum from the mixture of the second component as per step b) are formed on at least part of the surface.

The process of the invention is advantageous when the aluminum content of $Al^{\pm 0}$ in the mixture as per step b) is in the range from 90 to 99.5% by weight, based on the mixture.

The process of the invention is advantageous when $Al^{3+}$ is comprised in addition to $Al^{\pm 0}$ in the mixture as per step b).

The process of the invention is advantageous when the $Al^{3+}$ is present in the form of an oxidic compound selected from the group consisting of aluminum oxides, hydroxides and carbonates.

The process of the invention is advantageous when at least one organic compound or a further metal or metal oxide or metal carbonate is comprised in addition to $Al^{\pm 0}$ in the mixture as per step b), where the further metals are selected from the group consisting of Ni, Fe, Co, Cu, Cr, Pt, Ag, Au, Pd and Mo.

The process of the invention is advantageous when the first metal of the shaped metal foam body from step a) is selected from the group consisting of Ni, Co and Cu.

The invention further provides a shaped catalyst body obtainable by the process of the invention.

The invention further provides a process for producing an active catalyst fixed bed, comprising the following steps:

I) introduction of one or more shaped catalyst bodies obtainable by the process of the invention for producing shaped catalyst bodies into a reactor so as to form a stationary catalyst fixed bed, II) activation of the stationary catalyst fixed bed obtained after step I) with an aqueous base having a concentration of not more than 3.5% by weight.

The process of the invention for producing an activated catalyst fixed bed is advantageous when the active catalyst fixed bed obtainable according to step II) is treated with a washing agent selected from the group consisting of $C_1$-$C_4$-alkanols, water and mixtures thereof in an optional step III) and is subsequently brought into contact with a dopant selected from the group consisting of Ti, Ta, Zr, V, Cr, Mo, W, Mn, Re, Fe, Ru, Co, Rh, Ir, Ni, Pd, Pt, Cu, Ag, Au, Ce and Bi in a step IV).

The invention further provides the activated catalyst fixed bed obtainable by the process of the invention for producing an activated catalyst fixed bed.

The process of the invention for producing an activated catalyst fixed bed is advantageous when the shaped catalyst body in step I) is present in monolithic form.

The invention further provides for the use of the activated catalyst fixed bed according to the invention for hydrogenating hydrogenatable organic compounds which have at least one carbon-carbon double bond, carbon-nitrogen double bond, carbon-oxygen double bond, carbon-carbon triple bond, carbon-nitrogen triple bond or nitrogen-oxygen double bond.

The use according to the invention is advantageous when the organic compound used for the hydrogenation is 1,4-butynediol or n-butyraldehyde and, as a result of the hydrogenation, 1,4-butanediol is obtainable from the 1,4-butynediol and n-butanol is obtainable from the n-butyraldehyde.

The invention further provides for the use of the activated catalyst fixed bed according to the invention for the degradation of formates in formate-comprising mixtures, wherein the activated catalyst fixed bed comprises nickel as first metal in the shaped metal foam body from step a) of the shaped catalyst body and the formate degradation is carried out at a temperature of from 60 to 300° C. and a pressure of from 0.1 to 300 bar in the presence of hydrogen.

The use according to the invention of the activated catalyst fixed bed of the invention for the degradation of formates is advantageous when the formate-comprising mixture comprises carbonyl compounds which have been formed by an aldol reaction of alkanals with formaldehyde and/or corresponding hydrogenation products thereof.

The use according to the invention of the activated catalyst fixed bed of the invention for the degradation of formates is advantageous when the formate-comprising mixture comprises carbonyl compounds which have been formed by hydroformylation of alkanes by means of CO and $H_2$ and/or corresponding hydrogenation products thereof.

DESCRIPTION OF THE INVENTION

The process of the invention for producing shaped catalyst bodies will hereinafter also be referred to as "process 1" for short. The process of the invention for producing an active catalyst fixed bed obtainable from the shaped catalyst bodies with subsequent activation will hereinafter also be referred to as "process 2" for short. Unless explicitly stated otherwise in the following, information given in respect of suitable and preferred embodiments applies equally to process 1 and process 2.

Provision of a Shaped Metal Foam Body (Step a))

Shaped catalyst bodies or shaped metal foam bodies are used in processes 1 and 2 according to the invention. The generic term shaped body will be used here for both terms. For the purposes of the invention, the term shaped body encompasses both monolithic shaped bodies and also particulate shaped bodies. However, preference is given to monolithic shaped bodies. For the purposes of the invention, monolithic shaped bodies are structured shaped bodies which are suitable for producing static, structured catalyst fixed beds. In contrast to particulate catalysts, catalyst fixed beds which are essentially cohesive and free of joints can be produced from monolithic shaped bodies. This corresponds to the definition of monolithic in the sense of "consisting of one piece". The shaped catalyst bodies of the invention frequently display a higher ratio of axial flow (longitudinal flow) relative to radial flow (transverse flow) when, in the preferred embodiment, they are present as monolithic shaped catalyst bodies in contrast to disordered catalyst beds, e.g. composed of pellets. Monolithic shaped bodies correspondingly have channels in the flow direction of the reaction medium of the hydrogenation reaction. The particulate shaped bodies of the invention generally have the catalytically active sites in the fixed bed on an exterior surface. Preferred catalyst fixed beds according to the invention made up of monolithic shaped bodies have a plurality of channels, with the catalytically active sites being arranged on the surface of the channel walls. The reaction mixture of the hydrogenation reaction can flow through these channels in the flow direction through the reactor. This generally results in significantly better contacting of the reaction mixture with the catalytically active sites than in the case of disordered catalyst beds made up of particulate shaped bodies according to the invention. However, disordered catalyst beds composed of particular shaped bodies can also be employed in process 2 according to the invention.

The shaped bodies used according to the invention are either shaped bodies made up of individual catalyst bodies having a greatest longitudinal dimension in any direction of less than 1 cm. Such nonmonolithic shaped bodies lead to catalyst fixed beds in the form of customary disordered catalyst beds. In a preferred embodiment, the shaped bodies of the invention are present as monolithic shaped bodies and have a regular two-dimensional or three-dimensional structure and in this way differ from shaped bodies according to the invention in particle form, which can be used as loose random bed.

The preferred shaped bodies according to the invention, which are used as monolithic shaped bodies, have, based on the entire shaped body, a smallest dimension in one direction of preferably at least 1 cm, particularly preferably at least 2 cm, in particular at least 5 cm. The maximum value of the greatest dimension in one direction is in principle not critical and is generally determined by the production process for the shaped bodies. Thus, shaped bodies can, for example, be in the form of plate-like foam bodies which can have a thickness in the range from millimeters to centimeters, a width in the range from a few centimeters to several hundred centimeters and a length (as greatest dimension in one direction) of up to a number of meters.

The preferred monolithic shaped bodies used according to the invention can, in contrast to the loose materials according to the invention, preferably be joined by positive locking to form larger units or consist of units which are larger than the bulk materials according to the invention.

The preferred monolithic shaped bodies used according to the invention differ from particulate shaped bodies according to the invention or their supports generally also by being present in substantially fewer parts. Thus, a catalyst fixed bed can, when it is provided with the preferred monolithic shaped bodies of the invention, be used according to the invention in the form of a single shaped body. However, a plurality of shaped bodies, preferably monolithic shaped bodies, are generally used for producing a catalyst fixed bed. The preferred monolithic shaped bodies used according to the invention generally have elongated three-dimensional structures. The preferred monolithic shaped bodies used according to the invention generally have continuous channels running through them. The channels running through the bodies can have any geometry, for example they can be present in a honeycomb structure. Suitable preferred monolithic shaped bodies can also be produced by deformation of sheet-like support structures, for example by rolling up or bending the sheet-like structures to form three-dimensional bodies. Proceeding from sheet-like substrates, the exterior shape of the shaped bodies can easily be matched to given reactor geometries.

The preferred monolithic shaped catalyst bodies used according to the invention make it possible to produce catalyst fixed beds in which controlled flow through the catalyst fixed bed is possible. Movement of the preferred monolithic shaped bodies under the conditions of the catalyzed reaction, e.g. rubbing of the preferred monolithic shaped bodies against one another, is avoided. Due to the ordered structure of the preferred monolithic shaped bodies and the resulting catalyst fixed bed, improved opportunities for hydrodynamically optimized operation of the catalyst fixed bed are obtained.

The preferred monolithic shaped bodies used in the process of the invention are preferably present in the form of a foam, gauze, woven fabric, drawn-loop knit, formed-loop knit or a different monolith. For the purposes of the invention, the term monolithic catalyst also encompasses catalyst structures which are known as "honeycomb catalysts".

The catalyst fixed beds used according to the invention, which comprise the preferred monolithic shaped bodies according to the invention, preferably have, in any section in a plane normal to the flow direction (i.e. horizontal) through the catalyst fixed bed, not more than 5%, particularly preferably not more than 1%, in particular not more than 0.1%, of free area which is not constituent of the monolithic shaped body, based on the total area of the section. The area of the pores and channels which open at the surface of the monolithic shaped body is not included in this free area. The indicated figures for free area relate exclusively to sections through the catalyst fixed bed in the region of the monolithic shaped body and not any internals such as flow distributors.

For the preferred embodiment of monolithic shaped bodies, pores are, for the purposes of the invention, hollow spaces in the monolithic shaped bodies which have only an opening at the surface of the preferred monolithic shaped bodies. For the purposes of the invention, channels are hollow spaces in the monolithic shaped bodies according to the invention which have at least two openings at the surface of the monolithic shaped bodies.

When the catalyst fixed beds used according to the invention comprise monolithic shaped bodies which have pores and/or channels, then at least 90% of the pores and channels, particularly preferably at least 98% of the pores and channels, preferably have an area of not more than 3 $mm^2$ in any section in the plane normal to the flow direction through the catalyst fixed bed.

When the catalyst fixed beds used according to the invention comprise monolithic shaped bodies which have pores and/or channels, then at least 90% of the pores and channels, particularly preferably at least 98% of the pores and channels, preferably have an area of not more than 1 $mm^2$ in any section in the plane normal to the flow direction through the catalyst fixed bed.

When the catalyst fixed beds used according to the invention comprise monolithic shaped bodies which have pores and/or channels, then at least 90% of the pores and channels, particularly preferably at least 98% of the pores and channels, preferably have an area of not more than 0.7 $mm^2$ in any section in the plane normal to the flow direction through the catalyst fixed bed.

In the catalyst fixed beds according to the invention which comprise monolithic shaped bodies, preference is given to at least 95% of the reactor cross section, particularly preferably at least 98% of the reactor cross section, in particular at least 99% of the reactor cross section, being filled with monolithic shaped catalyst bodies over at least 90% of the length along the longitudinal axis of the reactor.

In a specific embodiment, the preferred shaped bodies are present in the form of a foam. Here, the monolithic shaped bodies can have any suitable exterior shape, for example cubic, cuboidal, cylindrical, etc. Suitable woven fabrics can be produced with different types of weave, e.g. plain weave, twill weave, braid weave, five-harness satin weave or other specialty weaves. Woven wire fabrics made of weavable metal wires, e.g. iron, spring steel, brass, phosphor bronze, pure nickel, Monel, aluminum, silver, nickel silver (copper-nickel-zinc alloy), nickel, chromium-nickel, chromium steel, stainless, acid-resistant and highly heat-resistant chromium-nickel steels and also titanium, are also suitable. The same applies to drawn-loop knits and formed-loop knits. It is likewise possible to use woven fabrics, drawn-loop knits or formed-loop knits made of inorganic materials, e.g. $Al_2O_3$ and/or $SiO_2$. Woven fabrics, drawn-loop knits or formed-loop knits made of polymers such as polyamides, polyesters, polyolefins (e.g. polyethylene, polypropylene), polytetrafluoroethylene, etc., are also suitable. The abovementioned woven fabrics, drawn-loop knits or formed-loop knits and also other sheet-like structured catalyst supports can be shaped to give larger three-dimensional structures, known as monoliths. It is likewise possible not to build up monoliths from sheet-like supports but instead produce them directly without intermediate stages, for example the ceramic monoliths which have flow channels and are known to those skilled in the art.

Monolithic shaped bodies as are described, for example, in EP-A 0 068 862, EP-A-0 198 435, EP-A 201 614, EP-A 448 884, EP 0 754 664 A2, DE 433 32 93, EP 2 764 916 A1 and US 2008/0171218 A1 are suitable.

The shaped bodies preferably comprise at least one element selected from among Ni, Fe, Co, Cu, Cr, Pt, Ag, Au and Pd. In a specific embodiment, the first metal of the shaped body is selected from the group consisting of Ni, Co and Cu. In a very particular embodiment, the shaped bodies comprise Ni. In a particular embodiment, the shaped bodies do not comprise any palladium. For the purposes of the present invention, this means that no palladium is actively added in the production of the shaped bodies, neither as catalytically active metal nor as promoter element nor for providing the shaped bodies which serve as support material.

The shaped metal foam body used in step a) can comprise promoters in addition to the metal of the first component. The promoters are in this case selected from the group consisting of Ti, Ta, Zr, V, Cr, Mo, W, Mn, Re, Fe, Ru, Co, Rh, Ir, Ni, Pd, Pt, Cu, Ag, Au, Ce and Bi.

The shaped bodies are preferably present in the form of a foam. Suitable foams are in principle metal foams having different morphological properties in respect of pore size and pore shape, layer thickness, mass per unit area, geometric surface area, porosity, etc. A metal foam having Ni, Cu and/or Co as first component preferably has a density in the range from 400 to 1500 $g/m^2$, a pore size of from 400 to 3000 μm, preferably from 400 to 800 μm, and a thickness in the range from 0.5 to 10 mm, preferably from 1.0 to 5.0 mm. It can be produced in a manner known per se. For example, a foam composed of an organic polymer can be coated with at least one first metal and the polymer can then be removed, e.g. by pyrolysis or dissolution in a suitable solvent, giving a metal foam. For coating with at least one first metal or a precursor thereof, the foam composed of the organic polymer can be brought into contact with a solution or suspension comprising the first metal. This can, for example, be effected by spraying or dipping. Deposition by means of chemical vapor deposition (CVD) is also possible. Thus, for example, a polyurethane foam can be coated with the first metal and the polyurethane foam can then be pyrolysed. A polymer foam suitable for producing shaped bodies in the form of a foam preferably has a pore size in the range from 100 to 5000 μm, particularly preferably from 450 to 4000 μm and in particular from 450 to 3000 μm. A suitable polymer foam preferably has a layer thickness of from 5 to 60 mm, particularly preferably from 10 to 30 mm. A suitable polymer foam preferably has a foam density of from 300 to 1200 $kg/m^3$. The specific surface area is preferably in the range from 100 to 20 000 $m^2/m^3$, particularly preferably from 1000 to 6000 $m^2/m^3$. The porosity is preferably in the range from 0.50 to 0.95.

In step b) of the process 1 according to the invention, a mixture is applied as second component to the surface of the shaped metal foam body. The mixture has an aluminum content in the form of $Al^{\pm 0}$ in the range from 80 to 99.8% by weight, based on the mixture. The mixture preferably has an aluminum content in the form of $Al^{\pm 0}$ in the range from 90 to 99.5% by weight, based on the mixture. Preference is given here to mixtures in which the aluminum particles have a particle size of not less than 5 μm and not greater than 200 μm. Particular preference is given to mixtures in which the aluminum particles have a particle size of not less than 5 μm and not greater than 75 μm. Apart from aluminum in the $Al^{\pm 0}$ form, it is advantageous for the mixture to additionally comprise aluminum in the form of $Al^{3+}$. This $Al^{3+}$ component is advantageously present in the form of oxidic compounds selected from the group consisting of aluminum oxides, hydroxides and carbonates. The proportion of $Al^{3+}$ is particularly preferably in the range from 0.05 to 10% by weight, very particularly preferably in the range from 0.1 to 8% by weight, based on the mixture. Apart from aluminum in the form of $Al^{\pm 0}$ and $Al^{3+}$, the mixture can also comprise organic compounds or a further metal or metal oxide or metal carbonate, with the further metals being selected from the group of promoters such as Ti, Ta, Zr, V, Cr, Mo, W, Mn, Re, Fe, Ru, Co, Rh, Ir, Ni, Pd, Pt, Cu, Ag, Au, Ce and Bi, with the organic compounds being selected from the group consisting of hydrocarbons, polymers, resins, amines and alcohols. When the surface of the shaped metal foam body from step a) of the process 1 according to the invention is impregnated with the mixture as per step b) and oxidic compounds of aluminum are comprised in the mixture, the mixture can be handled without problems in air and the reaction with water is greatly slowed. If the mixture in step b) of process 1 comprises too large an amount of oxidic components or intermetallic phases which are not leachable, the activated catalyst fixed bed obtainable by the process 2 has a lower activity in hydrogenations. The catalyst fixed bed which comprises shaped bodies which have been treated with a mixture which comprises too large an amount of oxidic components or has an aluminum content in the form of $Al^{\pm 0}$ of less than 80% by weight, based on the mixture, is thus less active. Thus, the solid catalyst bodies which have been produced by the process described in EP 2 764 91 comprise intermetallic compounds of Ni and Al before activation. These intermetallic compounds consist mainly of $NiAl_3$ (60% by weight of Al) and $Ni_2Al_3$ (40% by weight of Al). The $Al^{\pm 0}$ content thereof is significantly below 80% by weight. Although these shaped bodies can, after activation in a fixed bed, be used for hydrogenations, they are not very active. High space velocities cannot be achieved using such catalyst fixed beds. The activated catalyst fixed beds according to the invention obtainable by process 2 are several times more active, at the same high conversion, yield and selectivity. Thus, the catalyst fixed bed according to the invention can, for example in the hydrogenation of n-butyraldehyde, be operated at a 30 times higher space velocity than a catalyst bed comprising shaped bodies which have been produced by the process of EP 276491.

The application of the mixture as second component according to step b) of process 1 according to the invention can be carried out in many ways, e.g. by bringing the shaped body obtained from step a) into contact with the mixture as second component by rolling or dipping or applying the second component by spraying, sprinkling or pouring. For this purpose, the second component can be present in liquid form or preferably in the form of a powder.

The application of the aluminum of the mixture as per step b) of process 1 according to the invention to the shaped body is preferably carried out by impregnation of the shaped body provided in step a) with a binder (step b1)). The binder is an organic compound which assists adhesion of the mixture to the shaped body from step a). The binder is preferably selected from the group consisting of polyvinylpyrrolidone (PVP), waxes, ethylene glycol and mixtures of these compounds. The mixture as per step b) is applied to the shaped body which has been prepared in this way. As an alternative, the binder and the mixture can be applied in one step. For this purpose, the mixture and the binder are suspended in a liquid selected from the group consisting of water, ethylene glycol and PVP and optionally further additives. The binder itself is preferably liquid at room temperature, so that the additional liquid can be dispensed with and the mixture can be suspended in the binder itself. Particular preference is given to PVP as binder. The amount of polyvinylpyrrolidone is preferably from 0.1 to 15% by weight, particularly preferably from 0.5 to 10% by weight, based on the total weight of the suspension. The molecular weight of the polyvinylpyrrolidone is preferably in the range from 10 000 to 1 300 000 g/mol.

The impregnation can be carried out, for example, by spraying on the suspension or by dipping the shaped body into the suspension, but is not limited to these possibilities.

The alloy formation in step c) of process 1 according to the invention takes place under reducing conditions. For the purposes of the present invention, reducing conditions are the preferably stepwise heating-up in the presence of a gas mixture comprising hydrogen and at least one gas which is inert under the reaction conditions. As inert gas, preference is given to using nitrogen. For example, a gas mixture comprising 50% by volume of $N_2$ and 50% by volume of $H_2$ is suitable. The alloy formation can, for example, be carried out in a rotary tube furnace. Suitable heating rates are in the range from 1 to 10 K/min, preferably from 3 to 6 K/min. It can be advantageous to keep the temperature constant during heating-up. Thus, for example, the temperature can be kept constant at about 300° C., about 600° C. and/or about 700° C. during heating-up. The time for which the temperature is kept constant is preferably from about 1 to 120 minutes, particularly preferably from 5 to 60 minutes. The temperature is preferably kept constant in the range from 500 to 1200° C. during heating-up. If the temperature is kept constant a plurality of times, the last stage is preferably in the range from 500 to 1200° C. Furthermore, alloy formation preferably occurs during stepwise cooling. Cooling down to a temperature in the range from 150 to 250° C. is preferably carried out in the presence of a gas mixture comprising hydrogen and at least one gas which is inert under the reaction conditions. As inert gas, preference is given to using nitrogen. For example, a gas mixture comprising 50% by volume of $N_2$ and 50% by volume of $H_2$ is suitable. Further cooling is preferably carried out in the presence of at least one inert gas, preferably in the presence of nitrogen.

The weight of the shaped body in the form of a foam obtained after step c) is preferably from 25 to 80% higher, particularly preferably from 40 to 70% higher, than the weight of the shaped body from step a) used for the production thereof.

The temperature set depends on the metals and the phase diagram of the intermetallic phases to be obtained.

Suitable alloying conditions for step c) can be derived from the phase diagram of the participating metals, e.g. the phase diagram of Ni and Al. The proportion of Al-rich and leachable components such as $NiAl_3$ and $Ni_2Al_3$, for example, can be controlled in this way. In the shaped catalyst bodies obtained by the process of the invention, no Al—O compounds but only Al-comprising intermetallic phases, particularly preferably $Al_3Ni_2$ and $Al_3Ni$, are to be found in the X-ray diffraction pattern (XRD).

FIG. 1 shows, by way of example, an X-ray diffraction pattern for a shaped body after step b), produced using a mixture which has a total Al content of 86% by weight. 70% by weight thereof is present in the form of $Al^{\pm 0}$ and 16% is present in the form of $Al^{3+}$. Apart from Al and Ni and various intermetallic phases such as $Al_3Ni_2$, $Al_{1.1}Ni_{0.9}$, $AlNi_3$, it is also possible to discern $Al_2O_3$ in the diffraction pattern.

FIG. 2 shows, by way of example, an X-ray diffraction pattern in which a shaped body after step b), which had been produced using a mixture having a total Al content of 88% by weight of Al (74.6% of $Al^{\pm 0}$, 13.4% of $Al^{3+}$, was examined. This displays the following components: Ni, Al, $Al_3Ni_2$, $Al_{1.1}Ni_{0.9}$, $AlNi_3$.

FIG. 3 shows, by way of example, an X-ray diffraction pattern in which a shaped body after step b), which had been produced using a mixture having a total Al content of 99% by weight (97.9% of $Al^{\pm 0}$ and 1.1% of $Al^{3+}$), was examined. This displays the following components: Ni, Al, $Al_3Ni_2$, $Al_3Ni$.

Activation (=step II in process 2))

When the shaped body is used in the form of a monolithic shaped body or as random catalyst bed, the shaped bodies used for activation comprise, based on the total weight, from 20 to 80% by weight, particularly preferably from 30 to 7% by weight, of a first metal selected from among Ni, Fe, Co, Cu, Cr, Pt, Ag, Au and Pd.

The shaped bodies used for the activation preferably comprise, based on the total weight, from 20 to 80% by weight, particularly preferably from 30 to 70% by weight, of a second component which comprises Al in the form of $Al^{\pm 0}$ and in intermetallic phases with the first metal.

During the activation, the catalyst fixed bed from step I of process 2 is subjected to treatment with an aqueous base as treatment medium, with the second (leachable) component of the shaped catalyst bodies being at least partially dissolved and removed from the shaped catalyst bodies. The treatment with the aqueous base proceeds exothermically, so that the catalyst fixed bed heats up as a result of the activation. The heating of the catalyst fixed bed is dependent on the concentration of the aqueous base used. If no heat is removed from the reactor by active cooling but instead the heat is transferred to the treatment medium, so that an adiabatic mode of operation is realized to a certain extent, a temperature gradient is formed in the catalyst fixed bed during the activation, with the temperature increasing in the flow direction of the aqueous base. Even when heat is removed from the reactor by active cooling, a temperature gradient is formed in the catalyst fixed bed during the activation.

Preference is given to from 30 to 70% by weight, particularly preferably from 40 to 60% by weight, of the second component, based on the original weight of the said component, being removed from the shaped catalyst bodies by the activation.

Preference is given to the shaped catalyst bodies used for the activation comprising Ni and Al and from 30 to 70% by weight, particularly preferably from 40 to 60% by weight, of the Al, based on the original weight of the shaped body, being removed by the activation.

The determination of the amount of aluminum leached from the shaped catalyst bodies can, for example, be carried out by means of elemental analysis by the content of aluminum in the total amount of the loaded aqueous base discharged and of the washing medium being determined. As an alternative, the determination of the amount of aluminum leached from the shaped catalyst bodies can be determined via the amount of hydrogen formed during the course of the activation. In the case of aluminum being used, 3 mol of hydrogen are produced by leaching of 2 mol of aluminum.

The activation of a catalyst fixed bed according to process 2 according to the invention or in step II) can be carried out in the upflow or downflow mode. Preference is given to the upflow mode in which the fresh aqueous base is fed in at the bottom of the catalyst fixed bed and, after passage through the catalyst fixed bed, is discharged at the top.

After passage through the catalyst fixed bed, a loaded aqueous base is obtained. The loaded aqueous base has, compared to the aqueous base before passage through the catalyst fixed bed, a lower concentration of base and is enriched in the reaction products which have been formed in the activation and are at least partially soluble in the base. These reaction products include, for example, alkali metal aluminates, aluminum hydroxide hydrates, hydrogen, etc. (see, for example, U.S. Pat. No. 2,950,260).

The statement that the catalyst fixed bed has a temperature gradient during the activation means, for the purposes of the invention, that the catalyst fixed bed has this temperature gradient over the major part of the total activation time. The catalyst fixed bed preferably has a temperature gradient until at least 50% by weight, preferably at least 70% by weight, in particular at least 90% by weight, of the amount of aluminum to be removed has been removed from the shaped catalyst bodies. If the strength of the aqueous base used is not increased during the course of the activation and/or the temperature of the catalyst fixed bed is not increased by less cooling than at the beginning of the activation or by external heating, the temperature difference between the coldest place in the catalyst fixed bed and the hottest place in the catalyst fixed bed will become ever smaller during the course of the activation and can approach the value zero toward the end of the activation.

According to the invention, the temperature difference between the coldest place in the catalyst fixed bed and the hottest place in the catalyst fixed bed will be maintained at not more than 50 K. To determine the temperature difference over the catalyst fixed bed, the latter can be provided with conventional measuring devices for measuring the temperature. To determine the temperature difference between the hottest place in the catalyst fixed bed and the coldest place in the catalyst fixed bed, it is generally sufficient in the case of a reactor which is not actively cooled to determine the temperature difference between the place in the catalyst fixed bed which is farthest upstream and the place in the catalyst fixed bed which is farthest downstream. In the case of an actively cooled reactor, it can be useful to provide at least one further temperature sensor (e.g. 1, 2 or 3 further temperature sensors) between, in the flow direction, the place in the catalyst fixed bed which is farthest upstream and the place in the catalyst fixed bed which is farthest downstream.

The temperature difference between the coldest place in the catalyst fixed bed and the hottest place in the catalyst fixed bed is particularly preferably maintained at not more than 40 K, in particular not more than 25 K.

The temperature difference between the coldest place in the catalyst fixed and the hottest place in the catalyst fixed bed at the beginning of activation is preferably kept in the range from 0.1 to 50 K, preferably in the range from 0.5 to 40 K, in particular in the range from 1 to 25 K. It is possible to initially charge an aqueous medium without base at the beginning of the activation and then introduce fresh base until the desired concentration has been achieved. In this case, the temperature difference between the coldest place in the catalyst fixed bed and the hottest place in the catalyst fixed bed at the beginning of activation is considered to be the point in time at which the desired concentration of base at the reactor inlet has been reached for the first time.

In a reactor which is not actively cooled, the magnitude of the temperature gradient in the catalyst fixed bed can be controlled by selecting the amount and concentration of the aqueous base introduced as a function of the heat capacity of the medium used for activation. To control the magnitude of the temperature gradient in the catalyst fixed bed in the case of an actively cooled reactor, heat is additionally withdrawn by heat exchange from the medium used for activation. Such heat withdrawal can be effected by cooling of the medium used for activation in the reactor used and/or, if present, the liquid circulating stream.

According to the invention, the shaped catalyst bodies are subjected to treatment with aqueous base having a maximum concentration of 3.5% by weight in order to effect activation. The use of an aqueous base having a maximum concentration of 3.0% by weight is preferred. The shaped catalyst bodies are preferably subjected to treatment with an aqueous base having a concentration of from 0.1 to 3.5% by weight, particularly preferably an aqueous base having a concentration of from 0.5 to 3.5% by weight, to effect activation. The concentration stated is based on the aqueous base before contact with the shaped catalyst bodies. If the aqueous base is brought into contact the shaped catalyst bodies only once to effect activation, the concentration stated is based on the fresh aqueous base. If the aqueous base is conveyed at least partly in a liquid circulating stream to effect activation, fresh base can be added to the loaded base obtained after activation before renewed use for activating the shaped catalyst bodies. Here, the concentration values indicated above apply analogously.

The shaped catalyst bodies of Raney metal catalysts having a high activity and very good stability are obtained by adherence to the abovementioned concentrations for the aqueous base. This applies especially to activation of catalyst fixed beds for hydrogenation reactions on an industrial scale. Surprisingly, an excessive temperature increase and uncontrolled formation of hydrogen during activation of the catalysts is effectively avoided when using the concentration ranges indicated for the base. This advantage is especially apparent in the case of industrial-scale reactors.

In a preferred embodiment, the aqueous base used for activation is at least partly conveyed in a liquid circulating stream. In a first embodiment, the reactor comprising the catalyst to be activated is operated in the upflow mode. In the case of a vertical reactor, the aqueous base is then fed into the reactor at the bottom, conveyed from the bottom upward through the catalyst fixed bed, an output stream is taken off above the catalyst fixed bed and recirculated into the reactor at the bottom. Here, the stream discharged is preferably subjected to a work-up, e.g. by removal of hydrogen and/or discharge of part of the loaded aqueous base. In a second embodiment, the reactor comprising the catalyst to be activated is operated in the downflow mode. In the case of a vertical reactor, the aqueous base is then fed into the reactor at the top, conveyed from the top downward through the catalyst fixed bed, an output steam is taken off below the catalyst fixed bed and recirculated into the reactor at the top. Here, the stream discharged is preferably once again subjected to a work-up, e.g. by removal of hydrogen and/or discharge of part of the loaded aqueous base. The activation is preferably carried out in a vertical reactor in the upflow mode (i.e. with upward-directed flow through the catalyst fixed bed). Such a mode of operation is advantageous when even a small gas loading is produced by hydrogen formation during the activation, since this gas can more easily be discharged at the top.

In a preferred embodiment, fresh aqueous base is fed into the catalyst fixed bed in addition to the base conveyed in the liquid circulating stream. The introduction of fresh base can be carried out into the liquid circulating stream or separately therefrom into the reactor. The fresh aqueous base can be more concentrated than 3.5% by weight as long as the base concentration is not higher than 3.5% by weight after mixing with the recirculated aqueous base.

The ratio of aqueous base conveyed in the circulating stream to freshly introduced aqueous base is preferably in the range from 1:1 to 1000:1, particularly preferably from 2:1 to 500:1, in particular from 5:1 to 200:1.

The rate of introduction of the aqueous base (when the aqueous base used for activation is not conveyed in a liquid circulating stream) is preferably at most 5 l/min per liter of catalyst fixed bed, preferably not more than 1.5 l/min per liter of catalyst fixed bed, particularly preferably not more than 1 l/min per liter of catalyst fixed bed, based on the total volume of the catalyst fixed bed.

Preference is given to the aqueous base used for activation to be at least partly conveyed in a liquid circulating stream and the rate of introduction of the freshly introduced aqueous base being not more than 5 l/min per liter of catalyst fixed bed, preferably not more than 1.5 l/min per liter of catalyst fixed bed, particularly preferably not more than 1 l/min per liter of catalyst fixed bed, based on the total volume of the catalyst fixed bed.

The rate of introduction of the aqueous base (when the aqueous base used for activation is not conveyed in a liquid circulating stream) is preferably in the range from 0.05 to 5 l/min per liter of catalyst fixed bed, particularly preferably in the range from 0.1 to 1.5 l/min per liter of catalyst fixed bed, in particular in the range from 0.1 to 1 l/min per liter of catalyst fixed bed, based on the total volume of the catalyst fixed bed.

Preference is given to the aqueous base having a maximum concentration of 3.5% by weight which is used for activation to be conveyed at least partly in a liquid circulating stream and the rate of introduction of the freshly introduced aqueous base being in the range from 0.05 to 5 l/min per liter of catalyst fixed bed, particularly preferably in the range from 0.1 to 1.5 l/min per liter of catalyst fixed bed, in particular in the range from 0.1 to 1 l/min per liter of catalyst fixed bed, based on the total volume of the catalyst fixed bed.

This control of the rate of introduction of the fresh aqueous base is an effective way of keeping the temperature gradients which result in the catalyst fixed bed within the desired range of values.

The flow velocity of the aqueous base through the reactor comprising the catalyst fixed bed is preferably at least 0.5 m/h, particularly preferably at least 3 m/h, in particular at least 5 m/h, especially at least 10 m/h.

To avoid mechanical stressing and abrasion of the freshly formed porous catalyst metal, it can be useful to select a flow velocity which is not too high. The flow velocity of the aqueous base through the reactor comprising the catalyst fixed bed is preferably not more than 100 m/h, particularly preferably not more than 50 m/h, in particular not more than 40 m/h.

The flow velocities indicated above can be achieved particularly readily when at least part of the aqueous base is conveyed in a liquid circulating stream.

The base used for activating the catalyst fixed bed is selected from among alkali metal hydroxides, alkaline earth metal hydroxides and mixtures thereof. The base is preferably selected from among NaOH, KOH, and mixtures thereof. The base is preferably selected from among NaOH and KOH. Especially, NaOH is used as base. The base is used in the form of an aqueous solution for the activation.

Process 2 according to the invention for activating a catalyst fixed bed makes it possible to minimize dissolution of the catalytically active metal, e.g. nickel, effectively during the activation. When a liquid circulating stream is used, the metal content in the circulating stream is a suitable measure for the effectiveness of activation and the stability of the Raney metal catalyst obtained. The content of nickel in the loaded aqueous base or, if a liquid circulating stream is used for the activation, in the circulating stream during activation is preferably not more than 0.1% by weight, particularly preferably not more than 100 ppm by weight, in particular not more than 10 ppm by weight. The nickel content can be determined by means of elemental analysis. The same advantageous values are generally also achieved in the subsequent process steps, e.g. the treatment of the activated catalyst fixed bed with a washing medium, the treatment of the catalyst fixed bed with a dopant and the use in a hydrogenation reaction.

The processes of the invention make homogeneous distribution of the catalytically active Raney metal over the shaped bodies used and over all the activated catalyst fixed bed obtained possible. No gradient or only a small gradient in respect of the distribution of the catalytically active Raney metal in the flow direction of the activation medium through the catalyst fixed bed is formed. In other words, the concentration of catalytically active sites at the upstream end of the catalyst fixed bed is essentially the same as the concentration of catalytically active sites at the downstream end of the catalyst fixed bed. This advantageous effect is achieved particularly when the aqueous base used for activation is at least partly conveyed in a liquid circulating stream. The process of the invention also makes homogeneous distribution of the leached-out aluminum over the shaped bodies used and over all the activated catalyst fixed bed obtained possible. No gradient or only a small gradient in respect of the distribution of the leached-out aluminum in the flow direction of the activating medium through the catalyst fixed bed is formed.

A further advantage when the aqueous base used for activation is at least partly conveyed in a liquid circulating stream is that the amount of aqueous base required can be significantly reduced. Thus, a single pass of the aqueous base (without recirculation) and subsequent discharge of the loaded base leads to a high consumption of fresh base. The introduction of suitable amounts of fresh base into the recycle stream ensures that sufficient base for the activation reaction is always present. Overall, significantly smaller amounts are necessary for this purpose.

After passage through the catalyst fixed bed, a loaded aqueous base which has a lower base concentration compared to the aqueous base before passage through the catalyst fixed bed and which is enriched in the reaction products which are formed in the activation and are at least partially soluble in the base is obtained, as indicated above. At least part of the loaded aqueous base is preferably discharged. Thus, even when part of the aqueous base is conveyed in a circulating stream, excessive dilution and accumulation of undesirable impurities in the aqueous base used for the activation can be avoided. The amount of aqueous base which is freshly introduced per unit time preferably corresponds to the amount of loaded aqueous base discharged.

An output of loaded aqueous base is preferably taken off from the activation and subjected to a gas/liquid separation, giving a hydrogen-comprising gas phase and a liquid phase. The gas/liquid separation can be carried out using the apparatuses which are customary for this purpose and are known to those skilled in the art, e.g. conventional separation vessels. The hydrogen-comprising gas phase obtained in the phase separation can be discharged from the process and, for example, passed to thermal utilization. The liquid phase obtained in the phase separation, which comprises the discharged loaded aqueous base, is preferably at least partly recirculated as liquid circulating stream to the activation. Preference is given to discharging part of the liquid phase which is obtained in the phase separation and contains the discharged loaded aqueous base. Thus, as described above, excessive dilution and accumulation of undesirable impurities in the aqueous base used for activation can be avoided.

To monitor the progress of the activation and to determine the amount of aluminum leached from the shaped catalyst bodies, the amount of hydrogen formed during the course of the activation can be determined. Here, 3 mol of hydrogen are in each case produced by leaching of 2 mol of aluminum.

The activation according to the invention of a catalyst fixed bed in step II) of process 2 according to the invention is preferably carried out at a temperature of not more than 120° C., preferably at a temperature of not more than 100° C.

The activation according to the invention is preferably carried out at a pressure in the range from 0.1 to 10 bar, particularly preferably from 0.5 to 5 bar, especially at ambient pressure.

Treatment with a Washing Medium (=Step III))

In step III) of process 2 according to the invention, the activated catalyst fixed bed obtained in step II) is subjected to a treatment with a washing medium selected from among water, $C_1$-$C_4$-alkanols and mixtures thereof.

Suitable $C_1$-$C_4$-alkanols are methanol, ethanol, n-propanol, isopropanol, n-butanol and isobutanol.

The washing medium used in step III) preferably comprises water or consists of water.

The treatment with the washing medium in step III) is preferably carried out until the outflowing washing medium has a conductivity at 20° C. of not more than 200 mS/cm, particularly preferably not more than 100 mS/cm, in particular not more than 10 mS/cm.

Preference is given to using water as washing medium in step III) and carrying out the treatment with the washing medium until the outflowing washing medium has a pH at 20° C. of not more than 9, particularly preferably not more then 8, in particular not more than 7.

The treatment with the washing medium in step III) is preferably carried out until the outflowing washing medium has an aluminum content of not more than 5% by weight, particularly preferably not more than 5000 ppm by weight, in particular not more than 500 ppm by weight.

The treatment with the washing medium in step III) is preferably carried out at a temperature in the range from 20 to 100° C., particularly preferably from 20 to 80° C., in particular from 25 to 70° C.

Doping (=step IV)

The term doping refers to the introduction of foreign atoms into a layer or into the base material of a catalyst. The amount introduced in this procedure is generally small compared to the remaining catalyst material. Doping effects a targeted alteration of the properties of the starting material.

In a specific embodiment of process 2 according to the invention, the catalyst fixed bed is brought into contact with a dopant comprising at least one element which is different from the first metal and the Al of the second component of the shaped catalyst bodies used in step I) during and/or after the treatment in step III). Such elements will hereinafter be referred to as "promoter elements".

The use of promoter elements in hydrogenation catalysts such as Raney metal catalysts, for example to improve the yield, selectivity and/or activity of the hydrogenation and thus to improve the quality of the products obtained, has already been described in the literature. See: U.S. Pat. Nos. 2,953,604, 2,953,605, 2,967,893, 2,950,326, 4,885,410, 4,153,578, GB 2104794, U.S. Pat. Nos. 8,889,911, 2,948,687 and EP 2 764 916.

The use of promoter elements serves, for example, to avoid secondary reactions, e.g. isomerization reactions, or is advantageous for the partial or complete hydrogenation of intermediates. In general, the other hydrogenation properties of the doped catalyst are not adversely affected. The promoter elements can either be originally present in the alloy (the catalyst precursor) or are subsequently introduced into the shaped catalyst bodies.

The following four methods are in principle suitable for modifying the shaped catalyst bodies obtained by the process of the invention:

the promoter elements are present in the alloy for producing the shaped catalyst bodies (method 1),
the shaped catalyst bodies are brought into contact with a dopant during activation (method 2),
the shaped catalyst bodies are brought into contact with a dopant after activation (method 3),
the shaped catalyst bodies are brought into contact with a dopant during the hydrogenation and/or a dopant is introduced into the reactor during the hydrogenation (method 4).

Doping according to method 3 can be carried out before, during or after washing of the freshly activated catalyst.

The abovementioned method 1, in which the at least one promoter element is present in the alloy for producing the shaped catalyst bodies, is described, for example, in the abovementioned U.S. Pat. No. 2,948,687. Accordingly, a finely milled nickel-aluminum-molybdenum alloy is used for catalyst production in order to produce a molybdenum-comprising Raney nickel catalyst. The use of shaped catalyst bodies which comprise at least one promoter element is expressly permitted by the processes 1 according to the invention. In such a case, additionally bringing the catalyst fixed bed into contact with a dopant during and/or after the treatment in step III) of process 2 can generally be omitted.

The abovementioned method 2 is described, for example, in US 2010/0174116 A1 (=U.S. Pat. No. 8,889,911). According to this document, a doped catalyst which is modified with at least one promoter metal during and/or after activation is produced from an Ni/Al alloy. Here, the catalyst can optionally be subjected to a first doping even before activation. The promoter element used for doping by absorption on the surface of the catalyst during and/or after activation is selected from among Mg, Ca, Ba, Ti, Zr, Ce, Nb, Cr, Mo, W, Mn, Re, Fe, Co, Ir, Ni, Cu, Ag, Au, Bi, Rh and Ru. If the catalyst precursor is subjected to doping before activation, the promoter element is selected from among Ti, Ce, V, Cr, Mo, W, Mn, Re, Fe, Ru, Co, Rh, Ir, Pd, Pt and Bi.

The abovementioned method 3 is described, for example, in GB 2104794. This document concerns Raney nickel catalysts for the reduction of organic compounds, specifically the reduction of carbonyl compounds and the preparation of 1,4-butanediol from 1,4-butynediol. To produce these catalysts, a Raney nickel catalyst is subjected to doping with a molybdenum compound, which can be present in solid form, as a dispersion or as a solution. Other promoter elements such as Cu, Cr, Co, W, Zr, Pt or Pd can additionally be used. The method 3 is a particularly preferred method.

The abovementioned method 4 is described, for example, in U.S. Pat. Nos. 2,967,893 or 2,950,326. According to this document, copper in the form of copper salts is added in aqueous medium to a nickel catalyst for the hydrogenation of 1,4-butynediol.

According to EP 2 486 976 A1, supported activated Raney metal catalysts are doped subsequently with an aqueous metal salt solution.

The abovementioned EP 2 764 916 A1 teaches that promoter elements can be used in the production of foam-like shaped catalyst bodies. Doping can be carried out together with the application of the aluminum to the surface of a shaped metal foam body from step b) of process 1. Doping can also be carried out in a separate step subsequent to the activation as per step IV) in process 2.

The activity of a metal catalyst can also be influenced by doping in such a way that the hydrogenation stops at an intermediate stage. The use of a copper-modified palladium catalyst for the partial hydrogenation of 1,4-butynediol to 1,4-butenediol is known (GB832141). Thus, the activity and/or the selectivity of a catalyst can in principle be increased or reduced by doping with at least one promoter metal. Such doping should preferably not adversely affect the other hydrogenation properties of the doped catalyst. Such a chemical modification is also expressly permitted for processes 1 and 2 according to the invention.

One specific embodiment is a process for producing an active catalyst fixed bed (=process 2), wherein
   the shaped catalyst bodies used for activation, which the catalyst fixed bed comprises or of which the catalyst fixed bed consists, comprise at least one promoter element, and/or
   the catalyst fixed bed is brought into contact with a dopant comprising at least one promoter element during activation in step II), and/or
   the catalyst fixed bed is brought into contact with a dopant comprising at least one promoter element during and/or after treatment with a washing medium in step III), and/or
   the catalyst fixed bed is brought into contact with a dopant comprising at least one promoter element as per step IV) during the hydrogenation.

The dopant used according to the invention preferably comprises at least one promoter element selected from among Ti, Ta, Zr, V, Cr, Mo, W, Mn, Re, Fe, Ru, Co, Rh, Ir, Ni, Pd, Pt, Cu, Ag, Au, Ce and Bi.

It is possible for the dopant to comprise at least one promoter element which at the same time satisfies the definition of a first metal from step a) of process 1 as per the invention. Such promoter elements are selected from among Ni, Fe, Co, Cu, Cr, Pt, Ag, Au and Pd. In this case, the shaped body comprises, based on the reduced metallic form, a main amount (i.e. more than 50% by weight) of the first metal and a subordinate amount (i.e. less than 50% by weight) of a metal which is different therefrom as dopant. However, the total amount indicated for the first metal comprised by the shaped catalyst bodies encompasses all metals which satisfy the definition of a first metal as per the invention in their full proportion by weight (regardless of whether they function as hydrogenation active component or as promoter).

In a specific embodiment, the dopant does not comprise any promoter element which satisfies the definition of a first metal as per the invention. The dopant in this case preferably comprises exclusively a promoter element or more than one promoter element selected from among Ti, Ta, Zr, Ce, V, Mo, W, Mn, Re, Ru, Rh, Ir and Bi.

The dopant preferably comprises Mo as promoter element. In a specific embodiment, the dopant comprises Mo as sole promoter element.

The promoter elements are particularly preferably used in the form of their salts for doping. Suitable salts are, for example, the nitrates, sulfates, acetates, formates, fluorides, chlorides, bromides, iodides, oxides or carbonates. Due to their more noble character compared to Ni, the promoter elements either precipitate spontaneously in their metallic form or can be reduced to their metallic form by bringing into contact with a reducing agent such as hydrogen, hydrazine, hydroxylamine, etc. If the promoter elements are added during the activation operation, they can also be present in their metallic form. In this case, it can be useful to subject the catalyst fixed bed firstly to an oxidative treatment and subsequently to a reducing treatment after introduction of the promoter metals in order to form metal-metal compounds.

In a specific embodiment, the catalyst fixed bed is brought into contact with a dopant comprising Mo as promoter element in step IV) during and/or after the treatment with a washing medium in step III). More especially, the dopant comprises Mo as sole promoter element. Suitable molybdenum compounds are selected from among molybdenum trioxide, the nitrates, sulfates, carbonates, chlorides, iodides and bromides of molybdenum and the molybdates. The use of ammonium molybdate is preferred. In one preferred embodiment, a molybdenum compound which has good solubility in water is used. Here, good solubility in water means a solubility of at least 20 g/l at 20° C. When molybdenum compounds which have a relatively low solubility in water are used, it can be useful to filter the solution before the compounds are used as dopant. Water, polar solvents other than water which are inert toward the catalyst under the doping conditions and mixtures thereof are suitable as solvents for doping. The solvent used for doping is preferably selected from among water, methanol, ethanol, n-propanol, isopropanol, n-butanol, isobutanol and mixtures thereof.

The temperature during doping is preferably in the range from 10 to 100° C., particularly preferably from 20 to 60° C., in particular from 20 to 40° C.

The concentration of the promoter element in the dopant is preferably in the range from about 20 g/l to the maximum amount of the dopant which is soluble under the doping conditions. In general, the maximum amount will be taken to be a solution which is saturated at ambient temperature.

The duration of doping is preferably from 0.5 to 24 hours.

If doping is carried out during activation in step II) or as per step IV) during and/or after the treatment with a washing medium in step III), it can be advantageous for doping to be carried out in the presence of an inert gas. Suitable inert gases are, for example, nitrogen or argon.

In a specific embodiment for doping foam-like shaped catalyst bodies, a molybdenum source is dissolved in water and this solution is passed through the previously activated foam. When hydrates of ammonium molybdate, e.g. $(NH_4)_6Mo_7O_{24} \times 4\ H_2O$, are used, these are dissolved in water and this solution is used. The amount which can be used depends greatly on the solubility of the ammonium molybdate and is in principle not critical. In practice, less than 430 g of ammonium molybdate are dissolved per liter of water at room temperature (20° C.). If doping is carried out at a temperature higher than room temperature, larger amounts can also be used. The ammonium molybdate solution is subsequently passed over the activated and washed foam at a temperature of from 20 to 100° C., preferably at a temperature of from 20 to 40° C. The treatment time is preferably from 0.5 to 24 h, particularly preferably from 1 to 5 h. In a specific embodiment, the contacting is carried out in the presence of an inert gas such as nitrogen. The pressure is preferably in the range from 1 to 50 bar, especially at about 1 bar absolute. The doped Raney nickel foam can then be used for the hydrogenation either without further treatment or after having been washed again.

The doped shaped catalyst bodies preferably comprise from 0.01 to 10% by weight, particularly preferably from 0.1 to 5% by weight, of promoter elements, based on the reduced metallic form of the promoter elements and the total weight of the shaped catalyst bodies.

The catalyst fixed bed can comprise the promoter elements with an essentially homogeneous or heterogeneous distribution in terms of their concentration. In a specific embodiment, the catalyst fixed bed has a gradient of the concentration of the promoter elements in the flow direction. In particular, the catalyst fixed bed comprises or consists of shaped Ni/Al catalyst bodies which are activated according to the process of the invention and/or have been doped with Mo and have a gradient of the Mo concentration in the flow direction.

It is possible to obtain a fixed-bed catalyst which is installed in a fixed position in a reactor and comprises at least one promoter element which is essentially homogeneously distributed in terms of its concentration, i.e. is not present in the form of a gradient. To provide such a fixed-bed catalyst, it is possible to dope the shaped catalyst body which is not in installed form in the fixed-bed reactor itself, optionally with circulation, as a result of which a concentration gradient can be formed. The doping is then preferably carried out in an external vessel without circulation which is infinitely backmixed, e.g. a batch reactor without continuous input and output. After doping is complete and optionally after washing, such catalyst bodies can be installed in a fixed-bed reactor with or without circulation and are thus present without gradients.

To provide a catalyst fixed bed which has a gradient in the flow direction in respect of the concentration of the promoter elements, a liquid stream of the dopant can be passed through the catalyst fixed bed. When the reactor has a circulating stream, the dopant can, as an alternative or in addition, be fed in liquid form into the circulating stream. In the case of such a procedure, a concentration gradient of the promoter elements in the flow direction is formed over the entire length of the catalyst fixed bed. If it is desired that the concentration of the promoter element decreases in the flow direction of the reaction medium of the reaction to be catalyzed, the liquid stream of the dopant is passed through the catalyst fixed bed in the same direction as the reaction medium of the reaction to be catalyzed. If it is desired that the concentration of the promoter element increases in the flow direction of the reaction medium of the reaction to be catalyzed, then the liquid stream of the dopant is passed through the catalyst fixed bed in the opposite direction to the flow of the reaction medium of the reaction to be catalyzed.

In a first preferred embodiment, the activated catalyst fixed bed obtained by the process 2 according to the invention or the reactor provided after process 2 according to the invention which comprises such an activated catalyst fixed bed is employed for hydrogenating 1,4-butynediol to give 1,4-butanediol. It has surprisingly been found that a particularly high selectivity in the hydrogenation is achieved when a catalyst fixed bed made up of shaped Ni/Al catalyst bodies which after process 1 according to the invention comprise an appropriate aluminum content of $Al^{\pm 0}$ are activated as per process 2 according to the invention and/or have been doped with Mo and the concentration of molybdenum increases in the flow direction of the reaction medium of the hydrogenation reaction is used. The molybdenum content of the shaped catalyst bodies at the entry of the reaction medium into the catalyst fixed bed is preferably from 0 to 3% by weight, particularly preferably from 0 to 2.5% by weight, in particular from 0.01 to 2% by weight, based on metallic molybdenum and the total weight of the shaped catalyst bodies. The molybdenum content of the shaped catalyst bodies at the exit of the reaction medium from the catalyst fixed bed is preferably from 0.1 to 10% by weight, particularly preferably from 0.1 to 7% by weight, in particular from 0.2 to 6% by weight, based on metallic molybdenum and the total weight of the shaped catalyst bodies.

In a second preferred embodiment, the activated catalyst fixed bed obtained after process 2 according to the invention or the reactor provided after process 2 according to the invention which contains such an activated catalyst fixed bed is employed for hydrogenating n-butyraldehyde to give n-butanol. It has surprisingly been found that a particularly high selectivity in the hydrogenation is obtained when a catalyst fixed bed made up of shaped Ni/Al catalyst bodies which after process 1 according to the invention comprise an appropriate aluminum content of $Al^{\pm 0}$ and are activated as per process 2 according to the invention and/or have been doped with Mo and the concentration of molybdenum decreases in the flow direction of the reaction medium of the hydrogenation reaction is used. The molybdenum content of the shaped catalyst bodies at the entry of the reaction medium into the catalyst fixed bed is preferably from 0.5 to 10% by weight, particularly preferably from 1 to 9% by weight, in particular from 1 to 7% by weight, based on metallic molybdenum and the total weight of the shaped catalyst bodies. The molybdenum content of the shaped catalyst bodies at the exit of the reaction medium from the catalyst fixed bed is preferably from 0 to 7% by weight, particularly preferably from 0.05 to 5% by weight, in particular from 0.1 to 4.5% by weight, based on metallic molybdenum and the total weight of the shaped catalyst bodies.

It has been found that it is advantageous in terms of the efficiency of the doping of Raney metal catalysts and specifically Raney nickel catalysts with a promoter element, especially Mo, when the activated catalyst fixed bed is subjected to treatment with a washing medium (step III) after the activation (step II) and before doping (step IV). This applies particularly when foam-like Raney nickel catalysts are used for doping. It has been found, in particular, that the adsorption of molybdenum onto the shaped catalyst bodies is incomplete when the content of leachable aluminum is still too high after activation. For this reason, the treatment with a washing medium in step III) is preferably carried out until the outflowing washing medium has a conductivity of not more than 200 mS/cm at a temperature of 20° C. before doping in step IV). The treatment with the washing medium in step III) is preferably carried out until the outflowing washing medium has an aluminum content of not more than 500 ppm by weight.

The activated catalyst fixed beds obtained after process 2 according to the invention, which optionally comprise doped shaped catalyst bodies, generally display a high mechanical stability and long operating lives. Nevertheless, the fixed-bed catalyst is mechanically stressed when the components to be hydrogenated in the liquid phase flow through it. Wear or ablation of the outer layers of the active catalyst species can occur in the long term. If the Raney nickel foam catalyst has been produced by leaching and doping, then the metal element which has subsequently been introduced as dopant is then preferentially present on the outer active catalyst layers which can likewise be removed by mechanical liquid or gas stressing. If the promoter element is removed, this can result in a reduced activity and selectivity of the catalyst fixed bed. It has surprisingly been found that the original activity can be restored by carrying out the doping operation again. As an alternative, the dopant can also be added in the hydrogenation, with further doping then occurring in-situ (method 4).

Hydrogenation

For the purposes of the invention, hydrogenation is quite generally the reaction of an organic compound with addition of $H_2$ onto this organic compound. Functional groups are preferably hydrogenated to form the corresponding hydrogenated groups. This includes, for example, the hydrogenation of nitro groups, nitroso groups, nitrile groups or imine groups to form amine groups. It further includes, for example, the hydrogenation of aromatics to form saturated cyclic compounds. It further includes, for example, the hydrogenation of carbon-carbon triple bonds to form double bonds and/or single bonds. It further includes, for example, the hydrogenation of carbon-carbon double bonds to form single bonds. Finally, it includes, for example, the hydrogenation of ketones, aldehydes, esters, acids or anhydrides to form alcohols.

Preference is given to the hydrogenation of carbon-carbon triple bonds, carbon-carbon double bonds, aromatic compounds, compounds comprising carbonyl groups, nitriles and nitro compounds. Compounds which comprise carbonyl groups and are suitable for hydrogenation are ketones, aldehydes, acids, esters and anhydrides.

Particular preference is given to the hydrogenation of carbon-carbon triple bonds, carbon-carbon double bonds, nitriles, ketones and aldehydes.

The hydrogenatable organic compound is particularly preferably selected from among 1,4-butynediol, 1,4-butenediol, 4-hydroxybutyraldehyde, hydroxypivalic acid, hydroxypivalaldehyde, n-butyraldehyde and isobutyraldehyde, n-valeraldehyde and isovaleraldehyde, 2-ethylhex-2-enal, 2-ethylhexanal, nonanals, 1,5,9-cyclododecatriene, benzene, furan, furfural, phthalic esters, acetophenone and alkyl-substituted acetophenones. The hydrogenatable organic compound is very particularly preferably selected from among 1,4-butynediol, 1,4-butenediol, n-butyraldehyde and isobutyraldehyde, hydroxypivalaldehyde, 2-ethylhex-2-enal, nonanals and 4-isobutylacetophenone.

The use according to the invention of the activated catalyst fixed bed from process 2 leads to hydrogenated compounds which accordingly no longer comprise the group to be hydrogenated. If a compound comprises at least 2 different hydrogenatable groups, hydrogenation of only one of the unsaturated groups can be desired, e.g. when a compound has an aromatic ring and in addition a keto group or an aldehyde group. Such hydrogenations include, for example, the hydrogenation of 4-isobutylacetophenone to form 1-(4'-isobutylphenyl)ethanol or the hydrogenation of a C—C-unsaturated ester to form the corresponding saturated ester. In principle, an undesirable hydrogenation of other hydrogenatable groups, e.g. of carbon-carbon single bonds or of C—OH bonds to form water and hydrocarbons, can occur simultaneously with or instead of a hydrogenation in the sense of the invention. Such hydrogenations include, for example, the hydrogenolysis of 1,4-butanediol to form propanol or butanol. These latter hydrogenations generally lead to undesirable by-products and are therefore not wanted. The hydrogenation of the invention in the presence of an appropriately activated catalyst fixed bed preferably displays a high selectivity in respect of the desired hydrogenation reactions. These include, in particular, the hydrogenation of 1,4-butynediol or 1,4-butenediol to form 1,4-butanediol. They further include, in particular, hydrogenation of n-butyraldehyde and isobutyraldehyde to form n-butanol and isobutanol. They further include, in particular, the hydrogenation of hydroxypivalaldehyde or of hydroxypivalic acid to form neopentyl glycol. They further include, in particular, the hydrogenation of 2-ethylhex-2-enal to form 2-ethylhexanol. They further include, in particular, the hydrogenation of nonanals to form nonanols. They further include, in particular, the hydrogenation of 4-isobutylacetophenone to form 1-(4'-isobutylphenyl)ethanol.

The hydrogenation is preferably carried out continuously.

In the simplest case, the hydrogenation is carried out in a simple hydrogenation reactor. In a specific embodiment of the process of the invention, the hydrogenation is carried out in n hydrogenation reactors connected one after the other (in series) where n is an integer of at least 2. Suitable values for n are 2, 3, 4, 5, 6, 7, 8, 9 and 10. n is preferably from 2 to 6 and in particular 2 or 3. In this embodiment, the hydrogenation is preferably carried out continuously.

The reactors used for the hydrogenation can comprise an activated catalyst fixed bed which is formed by identical or different shaped catalyst bodies, but at least one activated catalyst fixed bed is that obtained after process 2 according to the invention. The activated catalyst fixed bed obtainable by process 2 can have one or more reaction zones. Differing reaction zones can have shaped catalyst bodies of differing chemical composition of the catalytically active species, with at least one shaped catalyst body corresponding to that comprised in the activated catalyst fixed bed after process 2. Different reaction zones can also have shaped catalyst bodies of the same chemical composition of the catalytically active species but in differing concentrations. If at least two reactors are used for the hydrogenation, the reactors can be identical or different reactors, but at least one reactor comprises the activated catalyst fixed bed obtainable by process 2. These can, for example, have identical or different mixing characteristics and/or be divided one or more times by internals.

Suitable pressure-rated reactors for the hydrogenation are known to those skilled in the art. They include the generally customary reactors for gas-liquid reactions, e.g. tube reactors, shell-and-tube reactors, gas recycle reactors, etc. One specific embodiment of the tube reactors is shaft reactors.

The process of the invention is carried out in the fixed-bed mode of operation. The fixed-bed mode of operation can, for example, be carried out in the upflow mode or in the downflow mode.

The reactors used for the hydrogenation comprise a catalyst fixed bed which has been activated as per process 2 according to the invention and through which the reaction medium flows. The activated catalyst fixed bed can be formed by a single type of shaped catalyst bodies or by various shaped catalyst bodies, but at least one shaped catalyst body corresponds to the shaped catalyst bodies which are comprised in the catalyst fixed bed after process 2 according to the invention. The catalyst fixed bed can have one or more zones, with at least one of the zones comprising a material which is active as hydrogenation catalyst. Each zone can comprise one or more different catalytically active materials and/or comprise one or more different inert materials. Different zones can each have identical or different compositions. It is also possible to provide a plurality of catalytically active zones which are, for example, separated from one another by inert beds or spacers. The individual zones can also have different catalytic activities. For this purpose, different catalytically active materials can be used and/or an inert material can be mixed into at least one of the zones. The reaction medium which flows through the catalyst fixed bed obtainable as per process 2 according to the invention comprises at least one liquid phase. The reaction medium can additionally comprise a gaseous phase.

The invention further provides for the use of the activated catalyst fixed beds according to the invention obtainable after process 2 for the degradation of formate-comprising mixtures. For the purposes of the invention, formate-comprising mixtures are, in particular, mixtures comprising carbonyl compounds which have been formed, for example, by an aldol reaction of alkanones or alkanals with formaldehyde, e.g. methylolalkanals, and also corresponding hydrogenation products thereof. These products comprise formates in addition to the abovementioned carbonyl compounds. For the purposes of the present invention, the term formate encompasses formic acid and salts thereof or esters of formic acid with alcohols. These formates comprise formic acid which is comprised in the formaldehyde used and/or is formed by the Cannizzaro reactions during the reaction with formaldehyde. A further variant of formate-comprising mixtures is mixtures comprising carbonyl compounds which have been formed by hydroformylation of alkenes, and also the corresponding hydrogenation products thereof. These mixtures also comprise formates or formic acid, the presence of which is based on the hydroformylation of carbonyl compounds or the hydrolysis of esters formed by subsequent reactions of the alkanals by means of water. Hydrogenation products are, in particular, those in which the aldehyde or keto group of the carbonyl compounds has been reduced to the alcohol.

These formates can interfere in the subsequent stages, for example by formation of CO during a hydrogenation or by esterification of the product, which can lead to decreases in yield or purity problems in the end product. Furthermore, the formates can, for example in the work-up by distillation, liberate formic acid which can then lead to undesirable corrosion and require the use of expensive materials.

It is therefore also an object of the present invention to provide a process by means of which formates comprised in mixtures can be degraded in their entirety or at least to an extent of 10%, preferably 30%, particularly preferably 50%.

This object is achieved by the use of the activated catalyst fixed bed according to the invention obtainable as per process 2 for the degradation of formates in formate-comprising mixtures, wherein the activated catalyst fixed bed comprises nickel as first metal in the shaped body from step a) of the shaped catalyst body and the formate degradation is carried out at a temperature of from 60 to 300° C. and a pressure of from 0.1 to 300 bar in the presence of hydrogen.

The formate degradation is carried out in the presence of hydrogen at a temperature in the range from 60 to 300° C., preferably in the range from 80 to 220° C., particularly preferably in the range from 100 to 180° C., and a pressure in the range from 0.1 to 300 bar, preferably in the range from 1 to 250 bar, particularly preferably in the range from 10 to 200 bar.

In the process of the invention, no CO but instead $CO_2$ and hydrogen are formed in the degradation of the formates. This hydrogen can be used for the hydrogenation of carbonyl groups. An advantage of the process of the invention is thus that no catalyst deactivation or poisoning by means of CO takes place.

The conversion in the hydrogenation is preferably at least 90 mol %, particularly preferably at least 95 mol %, in particular at least 99 mol %, especially at least 99.5 mol %, based on the total weight of hydrogenatable components in the starting material used for the hydrogenation. The conversion is based on the amount of the desired target compound obtained, regardless of the number of molar equivalents of hydrogen which have been taken up by the starting compound in order to arrive at the target compound. If a starting compound used in the hydrogenation comprises a plurality of hydrogenatable groups or comprises a hydrogenatable group which can take up a plurality of the equivalents of hydrogen (e.g. an alkyne group), the desired target compound can be either the product of a partial hydrogenation (e.g. alkyne to alkene) or a complete hydrogenation (e.g. alkyne to alkane).

For good mass transfer to take place in the shaped catalyst bodies, the velocity at which the reaction mixture flows through the activated catalyst fixed bed obtainable by process 2 according to the invention should not be too low. The flow velocity of the reaction mixture through the reactor comprising the activated catalyst fixed bed according to the invention is preferably at least 30 m/h, preferably at least 50 m/h, in particular at least 80 m/h. The flow velocity of the reaction mixture through the reactor comprising the activated catalyst fixed bed according to the invention is preferably not more than 1000 m/h, particularly preferably not more than 500 m/h, in particular not more than 400 m/h.

The flow direction of the reaction mixture is, especially in the case of an upright reactor, in principle not of critical importance. The hydrogenation can thus be carried out in the upflow mode or downflow mode. The upflow mode, in which the reaction mixture to be hydrogenated is introduced at the bottom of the catalyst fixed bed and, after passage through the activated catalyst fixed bed, is discharged at the top, can be advantageous. This applies particularly when the throughput of gas should be only low (e.g. <50 m/h). These flow velocities are generally achieved by part of the liquid stream leaving the reactor being recirculated, with the recirculated stream being combined with the feed stream either upstream of the reactor or else in the reactor. The feed stream can be introduced at a number of places over the length and/or the width of the reactor.

In a preferred embodiment, the reaction mixture of the hydrogenation is at least partly conveyed in a liquid circulating stream.

The ratio of reaction mixture conveyed in the circulating stream to freshly introduced feed stream is preferably in the range from 1:1 to 1000:1, more preferably from 2:1 to 500:1, in particular from 5:1 to 200:1.

Preference is given to an output being taken from the reactor and subjected to a gas/liquid separation, giving a hydrogen-comprising gas phase and a product-containing liquid phase. For the gas/liquid separation, it is possible to use the apparatuses which are customary for this purpose and are known to those skilled in the art, for example the customary separation vessels (separators). The temperature in the gas/liquid separation is preferably the same as or lower than the temperature in the reactor. The pressure in the gas/liquid separation is preferably the same as or lower than the pressure in the reactor. The gas/liquid separation is preferably carried out at essentially the same pressure as in the reactor. The pressure difference between reactor and gas/liquid separation is preferably not more than 10 bar, in particular not more than 5 bar. It is also possible for the gas/liquid separation to have a two-stage configuration. The absolute pressure in the second gas/liquid separation is then preferably in the range from 0.1 to 2 bar.

The product-comprising liquid phase obtained in the gas/liquid separation is generally at least partly discharged. The product of the hydrogenation can be isolated from this output, optionally after a further work-up. In a preferred embodiment, the product-comprising liquid phase is at least partly recirculated as liquid circulating stream to the hydrogenation.

The hydrogen-comprising gas phase obtained in the phase separation can be at least partly discharged as offgas. Furthermore, the hydrogen-comprising gas phase obtained in the phase separation can be at least partly recirculated to the hydrogenation. The amount of hydrogen discharged via the gas phase is preferably from 0 to 500 mol % of the molar amount of hydrogen consumed in the hydrogenation. For example, at a consumption of one mole of hydrogen, 5 mol of hydrogen can be discharged as offgas. The amount of hydrogen discharged by the gas phase is particularly preferably not more than 100 mol %, in particular not more than 50 mol %, of the molar amount of hydrogen consumed in the hydrogenation. The CO content in the gas phase in the reactor can be controlled by means of this discharge stream. In a specific embodiment, the hydrogen-comprising gas phase obtained in the phase separation is not recirculated. However, should this nevertheless be desired, the recirculated amount is preferably up to 1000% of the amount of gas required chemically for the reaction, particularly preferably up to 200%.

The gas throughput, expressed as the superficial velocity of gas at the reactor outlet, is generally below 200 m/h, preferably below 100 m/h, particularly preferably below 70 m/h, very particularly preferably below 50 m/h, under reaction conditions. The gas here consists essentially of hydrogen, preferably to an extent of at least 60% by volume. The gas velocity at the beginning of the reactor is extremely variable since hydrogen can also be introduced at intermediate feed points. However, if all hydrogen is to be added at the beginning, the gas velocity is generally higher than at the end of the reactor.

The absolute pressure in the hydrogenation is preferably in the range of 1 to 330 bar, particularly preferably in the range of 5 to 100 bar, in particular in the range from 10 to 60 bar.

The temperature in the hydrogenation is preferably in the range from 60 to 300° C., particularly preferably from 70 to 220° C., in particular from 80 to 200° C.

In a specific embodiment, the activated catalyst fixed bed obtainable by process 2 according to the invention has a temperature gradient during the hydrogenation. The temperature difference between the coldest place in the catalyst fixed bed and the hottest place in the catalyst fixed bed is preferably kept to not more than 50 K. The temperature difference between the coldest place in the catalyst fixed bed and the hottest place in the catalyst fixed bed is preferably kept in the range from 0.5 to 40 K, preferably in the range from 1 to 30 K.

The following examples serve to illustrate the invention without restricting it in any way.

EXAMPLES

Production Examples

Example 1

0.5 g of polyvinylpyrrolidone (molar mass: 40 000 Da) was dissolved in 29.5 g of deionized water and 20 g of a mixture comprising 98.9% by weight of Al (97.9% $Al^{\pm 0}$, 1% $Al^{3+}$) having a particle size of <25 µm were added. The suspension was stirred to effect homogenization. A nickel foam having an average pore size of 580 µm, a thickness of 1.9 mm and a weight per unit area of 1000 g/m$^2$ was then placed in the suspension. After impregnation, the excess suspension was carefully absorbed by means of a paper towel. The foam which had been coated in this way was heated at a heating rate of 5° C./min in 3 stages to 700° C. in a rotary tube furnace. The temperature was held at 300° C. and 600° C. for 30 minutes in each case. Heating up was carried out under a stream of gas consisting of 20 standard l/h of nitrogen and 20 standard l/h of hydrogen. The cooling phase was likewise carried out under this gas stream (20 standard l/h of $N_2$ and 20 standard l/h of $H_2$) down to a temperature of 200° C. The foam was then cooled further to room temperature using a stream of 100 standard l/h of nitrogen. The foam produced in this way displayed a weight increase of 42% compared to the nickel foam originally used.

Example 2

0.5 g of polyvinylpyrrolidone (molar mass: 40 000 Da) was dissolved in 29.5 g of deionized water and 20 g of aluminum powder (particle size <75 µm, total Al content 99% by weight (97.9% of $Al^{\pm 0}$, 1.1% of $Al^{3+}$)) were added. The further processing was carried out as described in Example 1. The foam produced in this way displayed a weight increase of 52% compared to the nickel foam originally used.

Example 3

0.5 g of polyvinylpyrrolidone (PVP, molar mass: 40 000 Da) was dissolved in 29.5 g of ethylene glycol and 20 g of a mixture comprising 98% by weight of Al (95.8% of $Al^{\pm 0}$, 2.2% of $Al^{3+}$) having a particle size of <75 μm were added. The suspension was subsequently shaken so as to form a homogeneous suspension. A nickel foam having an average pore size of 580 μm, a thickness of about 1.9 mm and a weight per unit area of about 1000 g/m$^2$ was then placed in the suspension and the suspension was shaken vigorously again. The foam which had been coated in this way was laid on a paper towel and the excess suspension was carefully dabbed off. The foam which had been coated in this way was heated at a heating rate of 5° C./min to 300° C. in a rotary tube furnace, then held at 300° C. for 30 minutes, heated further at 5° C./min to 500° C., held for 30 minutes and heated further at 5° C./min to 900° C. and held for 30 minutes. Heating was carried out under 20 standard l/h of nitrogen and 20 standard l/h of hydrogen. The cooling phase was likewise carried out under this gas stream (20 standard l/h of $N_2$ and 20 standard l/h of $H_2$) to a temperature of 200° C. The foam was then cooled further down to room temperature using a stream of 100 standard l/h of nitrogen. The foam produced in this way displayed a weight increase of 40% compared to the nickel foam originally used.

Example 4

A nickel foam having an average pore size of 580 μm, a thickness of about 1.9 mm and a weight per unit area of about 1000 g/m$^2$ was laid in a 0.1% strength, aqueous PVP solution (molar mass: 1 300 000). The foam was taken from the solution and dried in air at room temperature. The foam which had been impregnated in this way was treated with a mixture comprising 96% by weight of Al (91.5% of $Al^{\pm 0}$, 4.5% of $Al^{3+}$) having a particle size of <75 μm. To improve the adhesion, the mixture was rubbed mechanically on the surface. The foam was heated at a heating rate of 10 K/min to 700° C. in a stream of gas comprising 20 standard l/h of nitrogen and 20 standard l/h of hydrogen and held there for 20 minutes. Cooling was likewise carried out under 20 standard l/h of $N_2$ and 29 standard l/h of $H_2$ down to room temperature. The foam produced in this way displayed a weight increase of 41%.

Comparative Example 5

0.5 g of polyvinylpyrrolidone (molar mass: 40 000 Da) was dissolved in 29.5 g of deionized water and 20 g of a mixture comprising 86% by weight of Al (70% of $Al^{\pm 0}$, 16% of $Al^{3+}$) having a particle size of <5 μm was added. The suspension was subsequently shaken so as to form a homogeneous suspension. A nickel foam having an average pore size of 580 μm, a thickness of 1.9 mm and a weight per unit area of 1000 g/m$^2$ was then placed in the suspension and the suspension was shaken vigorously again. The foam which had been coated in this way was laid on a paper towel and the excess suspension was carefully dabbed off. The foam which had been coated in this way was heated at a heating rate of 5° C./min to 300° C. in a rotary tube furnace, then held at 300° C. for 30 minutes, heated further at 5° C./min to 500° C., held for 30 minutes and heated further at 5° C./min to 700° C. and held for 30 minutes. Heating was carried out under a stream of gas consisting of 20 standard l/h of nitrogen and 20 standard l/h of hydrogen. The cooling phase was likewise carried out under a stream of gas (20 standard l/h $N_2$ and 20 standard l/h $H_2$) down to a temperature of 200° C. The foam was then cooled further down to room temperature using a stream of 100 standard l/h of nitrogen. The foam produced in this way displayed a weight increase of 32% compared to the nickel foam originally used.

Comparative Example 6

0.5 g of polyvinylpyrrolidone (molar mass: 1 100 000 Da, Luvitec K85 BASF) was dissolved in 29.5 g of deionized water and 20 g of a mixture comprising 86% by weight of Al (70% of $Al^{\pm 0}$, 16% of $Al^{3+}$) having a particle size of <5 μm were added. Further processing was carried out as described in Comparative Example 6. The foam produced in this way displayed a weight increase of 40% compared to the nickel foam originally used.

Comparative Example 7

0.5 g of polyvinylpyrrolidone (molar mass: 40 000 Da) was dissolved in 29.5 g of deionized water and 20 g of a mixture comprising 88% by weight of Al (74.6% of $Al^{\pm 0}$, 13.4% of $Al^{3+}$) having a particle size of 30-50 μm were added. The further preparation was carried out as described under Comparative Example 6. The foam produced in this way displayed a weight increase of 39% compared to the nickel foam originally used.

Activity Test:

The foams produced in (Comparative) Examples 1 to 5 were activated by means of 30% strength NaOH solution at 60° C. for 30 minutes. After gas evolution ($H_2$) had abated, the mixture was cooled and the foams were washed with warm water (55° C.) until the washing solution had a pH of 7-8. The foams were dried in a stream of nitrogen. In order to test the activity, the foam was briefly exposed to oxygen. In the case of a positive test, the foam glows briefly (red heat) and becomes hot; in the case of a negative test, no or only very weak glowing and no or only very little heating of the foam can be detected.

TABLE 1

Overview of shaped bodies produced and results for these in the quick activity test

| (Comparative) Example | Polyvinylpyrrolidone | Size (μm) | Total aluminum Content (% by weight) | Gas evolution | Glowing in air |
|---|---|---|---|---|---|
| 1 | Mw = 40 000 Da | <25 | 98.9 | yes | yes |
| 2 | Mw = 40 000 Da | <75 | 99 | yes | yes |
| 3 | Mw = 40 000 Da in ethylene glycol | <75 | 98 | yes | yes |
| 4 | Mw = 1 300 000 Da | <75 | 96 | yes | yes |

TABLE 1-continued

Overview of shaped bodies produced and results for these in the quick activity test

| (Comparative) Example | Polyvinylpyrrolidone | Size (μm) | Total aluminum Content (% by weight) | Gas evolution | Glowing in air |
|---|---|---|---|---|---|
| 5 | Mw = 40 000 Da | <5 | 86 | yes | no |
| 6 | Mw = 1 100 000 Da, Luvitec K85 BASF | <5 | 86 | yes | no |
| 7 | Mw = 40 000 Da | 30-50 | 88 | yes | weak |

Use Examples

The starting materials used and products obtained were analyzed undiluted by means of conventional gas chromatography and a FID detector. The amounts indicated in the following are GC figures in % by area (water was not taken into account).

The formate content was in each case determined by ion exchange chromatography (IC). The following examples were carried out in a continuous hydrogenation apparatus consisting of a tube reactor, a gas-liquid separator, a heat exchanger and a circulating stream with a gear pump. The space velocities over the catalyst reported in the examples are based on the total volume occupied by the nickel-aluminum foams installed in the reactor.

Use Example 1: Hydrogenation of 1,4-butynediol (BID) to 1,4-butanediol (BDO)

Activation:

An apparatus comprising a tube reactor having an internal diameter of 25 mm was used. 35 ml of the nickel-aluminum foam from Production Example 1 was cut into round disks having a diameter of 25 mm using a laser cutter. The disks were stacked on top of one another and installed in the tube reactor. In order for the disks not to have any empty space between them and the reactor wall, a PTFE (polytetrafluoroethylene) sealing ring was installed after every 5 disks.

The reactor and the circulating stream were filled with deionized water and a 0.5% strength by weight NaOH solution was then fed in in the upflow mode and the catalyst fixed bed was activated at 100° C. over a period of 7 hours. The feed rate of the NaOH solution was 0.54 ml/min per ml of foam. The circulation rate was set to 18 kg/h, so that a feed-to-recycle ratio of 1:16 was obtained. The flow velocity of the aqueous base through the reactor was 37 m/h.

During the activation, no active Raney nickel in the form of fine free particles was detected in the circulating stream or in the reactor output. The elemental analysis of the activation solution gave a nickel content of less than 1 ppm. The aluminum content in the activation solution was about 3.8% at the beginning of the activation and decreased to 0.05% over the duration of the activation. The maximum temperature gradient of the catalyst fixed bed during activation was 10 K.

After activation for about 7 hours, the evolution of hydrogen decreased noticeably and the introduction of sodium hydroxide solution was stopped and the reactor was subsequently flushed with deionized water at 60° C. until a sample of the circulated liquid had a pH of 7.5 at 20° C. The flow rate of the deionized water was 380 ml/h at a circulation rate of 18 kg/h, i.e. a feed-to-recycle ratio of 1:47 was obtained. The flow velocity of the washing solution through the reactor was 37 m/h.

Doping:

An aqueous solution of 0.40 g of $(NH_4)Mo_7O_{24} \times 4\ H_2O$ in 20 ml of water was subsequently fed in in the downflow mode at 25° C. over a period of 1 hour. After all the solution had been introduced, the liquid was circulated by pumping in the circulating stream at a circulation rate of 15 kg/h for 3 hours.

Hydrogenation:

No BID solutions comprising more than 50% by weight of BID in water were used in the following. The aqueous BID starting material was prepared as described in Example 1 of EP 2 121 549 A1. The starting material was brought to a pH of 7.5 using sodium hydroxide solution and comprised, apart from BID and water, about 1% by weight of propynol, 1.2% by weight of formaldehyde and a series of other by-products in proportions of significantly less than 1% by weight.

The hydrogenation was carried out using an aqueous 50% strength by weight BID solution at 155° C., a hydrogen pressure of 45 bar of hydrogen and a space velocity over the catalyst of 0.5 $kg_{BID}/(l_{catalyst\ foam} \times h)$ at a circulation flow of 23 kg/h in the upflow mode. The hydrogenation gave 94.6% of BDO, 1.6% of n-butanol, 1.4% of methanol, 1.8% of propanol and 1900 ppm of 2-methylbutane-1,4-diol in the output over a period of 12 days. The space velocity over the catalyst was subsequently increased to 1.0 $kg_{BID}/(l_{catalyst\ foam} \times h)$ at the same circulation flow. The product stream consisted of (calculated on a water-free basis) 94.0% of BDO, 2.2% of n-butanol, 1.4% of methanol, 1.0% of propanol, 2000 ppm of 2-methylbutane-1,4-diol and about 1% of further secondary components.

Use Example 2: Hydrogenation of n-butyraldehyde (n-BA)

Activation and Doping:

The apparatus comprising a tube reactor having an internal diameter of 25 mm was again used. 35 ml of the nickel-aluminum foam from Production Example 2 was cut into round disks having a diameter of 25 mm using a laser cutter. The further activation and molybdenum doping were carried out as described in Use Example 1. After doping, the reaction system was emptied and the water was replaced by n-butanol.

Hydrogenation:

Using a method analogous to Use Example 1, n-butyraldehyde containing about 1500 ppm of isobutyraldehyde was hydrogenated over the nickel-aluminum foam. The hydrogenation was carried out at 140° C., a hydrogen pressure of 40 bar of hydrogen and varying space velocities over the catalyst at a circulation flow of 16 kg/h in the upflow mode. The molar ratio of hydrogen to the butyraldehyde was 1.1:1. The hydrogenation using the nickel-aluminum foams gives a conversion and a BuOH content in the output as reported in Table 2. The main secondary components consisted predominantly of isobutanol (1000-1500 ppm), butyl butyrate (100-300 ppm), dibutyl ether (50-300 ppm), ethylhexanediol (500-1500 ppm) and n-butyraldehyde dibutyl acetal (acetal, 100-1000 ppm):

TABLE 2

Hydrogenation results using the shaped bodies produced in the hydrogenation of n-butyraldehyde

| Foam from (Comparative) Example | Space velocity over the catalyst (kg/(l*h)) | Conversion (%) | n-Butanol (GC % by area) |
|---|---|---|---|
| 2 | 0.7 | >99.9 | 99.71 |
| 2 | 1.4 | >99.9 | 99.70 |
| 2 | 2.8 | >99.9 | 99.68 |
| 2 | 30.0 | 93.8 | 93.57 |
| 5 | 0.7 | 50 | 45 |
| 7 | 0.7 | 99.8 | 99.5 |
| 7 | 2.8 | 55 | 51 |

Use Example 3: Hydrogenation of Nonanal and Formate Decomposition

Activation and Doping:

The apparatus comprising a tube reactor having an internal diameter of 25 mm was again used. 35 ml of the nickel-aluminum foam from Production Example 3 was cut into round disks having a diameter of 25 mm using a laser cutter. The further activation and molybdenum doping were carried out as described in Use Example 1.

Hydrogenation:

Using a method analogous to Use Example 1, nonanal comprising about 1500 ppm of formate was hydrogenated over the nickel-aluminum foam from Production Example 3. After molybdenum doping, the reaction system was emptied and the water was replaced by n-nonanol. The hydrogenation was carried out at 140° C., a hydrogen pressure of 40 bar of hydrogen and a space velocity over the catalyst of 0.7 $kg_{nonanal}/(l_{catalyst\,foam} \times h)$ at a circulation flow of 16 kg/h in the upflow mode. The molar ratio of hydrogen to nonanal was 1.1:1. The hydrogenation gave 88.0% of nonanol (n and iso) in the output (according to GC analysis in % by area) over a period of 9 days. In addition, 5.8% of octanes and 6.1% of high boilers were present as main secondary components. The formate content had been reduced from 1500 ppm in the feed to 8 ppm in the output.

Use Example 4: Hydrogenation of Hydroxypivalaldehyde (HPA) and Formate Decomposition Activation and Doping:

The apparatus comprising a tube reactor having an internal diameter of 25 mm was again used. 35 ml of the nickel-aluminum foam from Production Example 2 was cut into round disks having a diameter of 25 mm using a laser cutter. The further activation and molybdenum doping were carried out as described in Use Example 1.

Hydrogenation:

Using a method analogous to Use Example 1, 15% by weight of hydroxypivalaldehyde in aqueous neopentyl glycol (NPG, 24% by weight) was hydrogenated over the nickel-aluminum foam from Production Example 2. The formate concentration in the feed was about 1700 ppm and the formaldehyde concentration was 1.4%. After molybdenum doping, the reaction system was emptied and the water was replaced by aqueous neopentyl glycol (NPG). The hydrogenation was carried out at 140° C., a hydrogen pressure of 40 bar of hydrogen and a space velocity over the catalyst of 0.5 $kg_{HPA}/(l_{catalyst\,foam} \times h)$ at a circulation flow of 5 kg/h in the upflow mode. The hydrogenation gave 94.8% of NPG in the output (according to GC analysis in % by area) over a period of 5 days. In addition, 1.6% of isobutanol. 1.6% of methanol and 0.88% of hydroxypivalaldehyde neopentyl glycol ester were present as main secondary components. The formate content in the output had been reduced to <100 ppm.

The invention claimed is:

1. A process for producing a shaped catalyst body, comprising the following steps:
    a) provisioning a shaped metal foam body comprising at least one first metal selected from the group consisting of Ni, Fe, Co, Cu, Cr, Pt, Ag, Au, and Pd, and
    b) impregnating the surface of the shaped metal foam body with
        b1) a binder, and
    subsequently or simultaneously, with a mixture as a second component, wherein the mixture comprises from 80 to 99.8% by weight of $Al^{\pm 0}$, based on the mixture, and
    c) thermally treating under reducing conditions the impregnated shaped metal foam body obtained in step b) so that intermetallic phases in the form of alloys of the metal of the shaped metal foam body from step a) and the aluminum from the mixture of the second component as per step b) are formed on at least part of the surface.

2. The process according to claim 1, wherein the aluminum content of the $Al^{\pm 0}$ in the mixture of step b) is in the range from 90 to 99.5% by weight, based on the mixture.

3. The process according to claim 1, wherein $Al^{\pm 0}$ is comprised in addition to $Al^{3+}$ in the mixture of step b).

4. The process according to claim 3, wherein the $Al^{3+}$ is present in the form of an oxidic compound selected from the group consisting of aluminum oxides, hydroxides, and carbonates.

5. The process according to claim 1, wherein at least one organic compound or a further metal or metal oxide or metal carbonate is comprised in addition to the $Al^{\pm 0}$ in the mixture of step b), wherein the further metals are selected from the group consisting of Ni, Fe, Co, Cu, Cr, Pt, Ag, Au, Pd, and Mo.

6. The process according to claim 1, wherein the first metal of the shaped metal foam body from step a) is selected from the group consisting of Ni, Co, and Cu.

7. The shaped catalyst body obtained according to claim 1.

8. A process for producing an active catalyst fixed bed, comprising the following steps:
    I) introducing one or more shaped catalyst bodies obtainable by the process according to claim 1 into a reactor so as to form a stationary catalyst fixed bed, and
    II) activating the stationary catalyst fixed bed obtained after step I) with an aqueous base having a concentration of not more than 3.5% by weight.

9. The process according to claim 8, wherein the active catalyst fixed bed obtainable according to step II) is treated with a washing agent selected from the group consisting of $C_1$-$C_4$-alkanols, water, and mixtures thereof in an optional step III), and is subsequently brought into contact with a dopant selected from the group consisting of Ti, Ta, Zr, V, Cr, Mo, W, Mn, Re, Fe, Ru, Co, Rh, Ir, Ni, Pd, Pt, Cu, Ag, Au, Ce, and Bi in a step IV).

10. An activated catalyst fixed bed obtained by the process according to claim 8.

11. The process according to claim 8, wherein the shaped catalyst body as per step I) is present in monolithic form.

12. A method of using the activated catalyst fixed bed according to claim 8, the method comprising hydrogenating hydrogenatable organic compounds that have at least one carbon-carbon double bond, carbon-nitrogen double bond, carbon-oxygen double bond, carbon-carbon triple bond, carbon-nitrogen triple bond, or nitrogen-oxygen double bond.

13. The method according to claim 12, wherein the organic compound used for the hydrogenation is 1,4-butynediol or n-butyraldehyde and, as a result of the hydrogenation, 1,4-butanediol is obtainable from the 1,4-butynediol and n-butanol is obtainable from the n-butyraldehyde.

14. The method of claim 8 further comprising the step of
III) using the activated catalyst fixed bed obtained after step II) to degrade formates in a formate-comprising mixtures, wherein the activated catalyst fixed bed comprises nickel as first metal in the shaped metal foam body from step a) of the shaped catalyst body, and the formate degradation is carried out at a temperature of from 60 to 300° C. and a pressure of from 0.1 to 300 bar in the presence of hydrogen.

15. The method according to claim 14, wherein the formate-comprising mixture comprises carbonyl compounds that have been formed by an aldol reaction of alkanals with formaldehyde and/or corresponding hydrogenation products thereof.

16. The method according to claim 14, wherein the formate-comprising mixture comprises carbonyl compounds that have been formed by hydroformylation of alkanes by means of CO and $H_2$ and/or corresponding hydrogenation products thereof.

* * * * *